(12) United States Patent
Halachmi Katchanov

(10) Patent No.: US 8,510,985 B2
(45) Date of Patent: Aug. 20, 2013

(54) ENERGY PRODUCTION FROM ALGAE IN PHOTO BIOREACTORS ENRICHED WITH CARBON DIOXIDE

(76) Inventor: Eliezer Halachmi Katchanov, Oranit (IL)

( * ) Notice: Subject to any disclaimer, the term of this patent is extended or adjusted under 35 U.S.C. 154(b) by 291 days.

(21) Appl. No.: 12/786,864

(22) Filed: May 25, 2010

(65) Prior Publication Data

US 2010/0233787 A1 Sep. 16, 2010

Related U.S. Application Data

(63) Continuation-in-part of application No. 12/177,298, filed on Jul. 22, 2008, now abandoned.

(51) Int. Cl.
*A01H 13/00* (2006.01)
(52) U.S. Cl.
USPC ............................................. 47/1.4
(58) Field of Classification Search
USPC ............................................. 47/1.4
See application file for complete search history.

(56) References Cited

U.S. PATENT DOCUMENTS

| | | | |
|---|---|---|---|
| 5,659,977 | A | 8/1997 | Jensen |
| 6,477,841 | B1 | 11/2002 | Yantovsky |
| 7,905,049 | B2 * | 3/2011 | Erd ................... 47/1.4 |
| 2002/0194782 | A1 | 12/2002 | Paisley |
| 2007/0048859 | A1 | 3/2007 | Sears |
| 2009/0301399 | A1 * | 12/2009 | Brown et al. ............... 119/226 |
| 2010/0018214 | A1 | 1/2010 | Halachmi Katchanov |
| 2011/0245552 | A1 * | 10/2011 | Hassan et al. .............. 585/240 |

FOREIGN PATENT DOCUMENTS

| | | |
|---|---|---|
| WO | 95/24548 | 9/1995 |
| WO | 00/57105 | 9/2000 |
| WO | 2007047805 | 4/2007 |

OTHER PUBLICATIONS

International Search Report of the International Searching Authority for PCT/IL2009/000712, issued on Jan. 4, 2010.
Written Opinion of the International Searching Authority for PCT/IL2009/000712, issued on Jan. 4, 2010.
Zhang Y., et al. "Experimental Study on Sequestrating of CO2 in the True Flue Gas by Ammonia Spray and Producing NH4HCO3", a presentation, Shenyang, China.

* cited by examiner

*Primary Examiner* — Kristen C Hayes
(74) *Attorney, Agent, or Firm* — Pearl Cohen Zedek Latzer, LLP

(57) ABSTRACT

A cyclic system composed of several integrated cyclic processes and a method for production of cement and or quicklime, ammonia, desalinated water and an excess of algae cells. The system comprises of: at least cement/quicklime production plant, at least ammonia production plant, at least one water desalination unit, at least one photo bioreactor. The energy source of the system is sunlight energy. The $CO_2$ produced by the system and other waste products are sequestrated and recycled for additional cycles of system operation. No $CO_2$ is released to the atmosphere. The system produces a huge excess of algae cells that accumulates in arithmetic or geometrical progression. The excess of algae cells can fuel additional energy consuming plants attached to the system or can be used for other various purposes such as food and food additives.

2 Claims, 15 Drawing Sheets

ENERGY PRODUCTION FROM ALGAE IN PHOTO BIOREACTORS ENRICHED WITH CARBON DIOXIDE

FIELD OF THE INVENTION

The present invention generally relates to the field of cement/quicklime production, ammonia production, water desalination and electric power production by sunlight energy mediated by algae cell.

BACKGROUND OF THE INVENTION

A presentation titled "Experimental study on sequestrating of $CO_2$ in the true flue gas by ammonia spray and producing $NH_4HCO_3$ by Zhang, Y., Li, Z.-Z., Li, C.-Z., Dong, J.-X. and Wang, Y. from the National Power Plant Combustion Engineering Research Center, Shenyang, China, is incorporated herein by reference in its entirety.

U.S. Pat. No. 6,477,841, which is incorporated herein by reference in its entirety, discloses a closed cycle power plant for conversion of solar to electrical energy has water tank for growing macroalgae and fluidized bed combustion chamber for combusting macroalgae in presence of oxygen and carbon dioxide.

EP0561436B1, which is incorporated herein by reference in its entirety, discloses a process for making cement by preheating the raw meal in a cyclone heater, calcining the preheated raw meal, burning the calcined raw meal in a rotary kiln, cooling the cement clinker formed in the rotary kiln and grinding the cement klinker.

US20020194782, which is incorporated herein by reference in its entirety, discloses an integrated biomass gasification and fuel cell system wherein the electrochemical reaction in the fuel cell is effected by providing the reactant gases from a gasifier.

WO2000057105, which is incorporated herein by reference in its entirety, discloses a closed cycle power plant for the conversion of solar energy stored by photosynthesis to electrical energy, comprising a body of water for growing macroalgae therein, and a fluidized bed combustion chamber for at least partial combustion of partially dried macroalgae having a water content of up to 60% wt/wt, the combustion being carried out in an artificial atmosphere of oxygen and carbon dioxide.

WO1995024548, which is incorporated herein by reference in its entirety, discloses an internal combustion engine comprising combustion chamber means, inlet track means, for directing air into the combustion chamber means, and fuel induction means, for supplying powdered fuel to be burned in the combustion chamber means, in which the fuel induction means are arranged for supplying the powdered fuel into the inlet track means, so that the so supplied powdered fuel forms a substantially homogenous fuel/air mixture for ignition in the combustion chamber means, during the engine's operation.

U.S. Pat. No. 5,659,977, which is incorporated herein by reference in its entirety, discloses an integrated plant including a microalgae production plant for growing, harvesting and drying algae and a fossil fuel-motor-generator plant producing electrical energy. A fossil fuel engine produces hot exhaust gas from which sensible heat dries the algae. The drying may be direct from the exhaust gas or may be indirect with the hot exhaust gas exchanging sensible heat with a recirculating stream of inert gas. Carbon dioxide from the exhaust gas is recovered for use as a nutrient in the microalgae production plant. Electrical energy from the generator is used to drive motors and/or produce artificial illumination and/or drive pumps, motors and controls in the microalgae production plant.

U.S. Pat. No. 6,477,841, which is incorporated herein by reference in its entirety, discloses a method for the conversion of solar energy stored by photosynthesis to electrical energy, utilizing a closed cycle power plant comprising a body of water for growing macroalgae therein, and providing a fluidized bed combustion chamber for at least partial combustion of partially dried macroalgae having a water content of up to 60% wt/wt, the combustion being carried out in an artificial atmosphere of oxygen and carbon dioxide.

WO2007047805, which is incorporated herein by reference in its entirety, discloses a device and method for carbon dioxide sequestering involving the use of a photo-bioreactor with Light Emitting Diodes (LED's) for the cost-effective photo-fixation of carbon dioxide ($CO_2$). This device and method is useful for removing undesirable carbon dioxide from waste streams.

BRIEF SUMMARY

The system comprises a basic core of three cyclic processes, synergistically integrated. These three cycles supply energy, raw materials and products to each other. To this basic core additional cyclic processes can be added in such a way that they use the energy and the products produced by the basic core to produce additional products by these attached cycles. The basic core produces by sunlight energy: cement/quicklime, a huge excess of chemical energy (fuel), ammonia and in addition, by the same amount of sunlight energy—a huge amount of desalinated water. The system fully recycles its carbon source and nitrogen source, without emitting them outside the system.

Each cyclic process is composed of an array of photo bioreactors. This array produces algae cells which serve as fuel to supply the energy needed to produce the products. The array collects the flue gases produced by the combustion of the algae cells and recycles the combustion products in order to produce the same amount of algae cells for an additional cycle of algae cells combustion.

The products of the basic core are:
1. Cement/quicklime
2. Desalinated water
3. Ammonia
4. An access of algae cells that can be used as a source of energy (combusted cells as fuel), or for additional various purposes such as: agricultural products, food additives, etc.

These Four Products can be Produced Only by the Synergistic Arrangement of the Cycles Described Below.

The Cycles of the Basic Core are:
The Cement/Quicklime Cycle:

The cement production is a heavily polluting $CO_2$ process and one of the most intensive energy consuming industries. In this system no $CO_2$ is emitted from the system to the atmosphere and sunlight is the energy source. A certain amount of algae cells are harvested from the photo bioreactors, dried and combusted in a kiln in which limestone is fired to produce cement or quicklime. The flue gases with the combustion products flow back to the array of the photo bioreactors for recycling and production of an additional amount of algae cells, which is also aimed for combustion in the kiln. The flue gases contain oxidized nitrogen (nitrates and nitrites) that can be used as a source of nitrogen for the algae cells. The amount of $CO_2$ in the flue gases includes the $CO_2$ produced by the combustion of the algae cells, and the $CO_2$ released from limestone during firing. This amount of $CO_2$ is about 3.44 fold higher than the amount of $CO_2$ that was produced by the algae cells combustion. This additional amount can be used to produce an amount of algae cells which is 3.44 fold higher than the amount of algae cells that is used for limestone firing, but an additional amount of available nitrogen source has to be added to this cycle since the amount of oxidized nitrogen can support the production of the amount of algae cells which at the most is equal to the amount of the cells that are combusted in the kilns. The required additional amount of nitrogen is supplied by the Ammonia Cycle.

The Ammonia Cycle:
The energy required for ammonia production in the existing plants is supplied by fossil fuels. In this system this energy is supplied by combustion of dried algae cells. The algae cells for the ammonia production can be allocated from the excess of the algae cells which are produced by the excess of $CO_2$ released from the limestone in the Cement/Quicklime Cycle. The amount of energy required to produce the amount of ammonia required for the production of the excess of algae cells is only 24% of the combusted energy content of the excess. Hence, only 24% of the excess has to be allocated for the ammonia production, and most of the excess (76%) remains for additional purposes. Actually, the amount of algae cells allocated from the excess of the algae cells is supposed to be much smaller. The flue gas produced by combustion of the algae cells in the ammonia plant are not released to the atmosphere but are also collected and recycled in the photo bioreactors array. Thus, an additional cycle of ammonia production is produced, in which an amount of algae cells which is equal to the amount of cells combusted in the ammonia plant is produced by the combustion products. By upscale of the ammonia plant—an additional amount of ammonia can be supplied for other purposes (fertilizers production, etc.).

The Cells Drying/Water Desalination Cycle:
The algae cells, after being harvested, are dried in an array of heat exchangers. The heat energy for cells drying is supplied by the hot flue gases which are produced in the combustion chamber while they flow back to the photo bioreactors. The wet algae cells moving in the opposite direction are used to cool the flue gases. The energy calculations show that an additional energy is required to dry the excess of algae cells produced by the system. This energy is produced by a separate drying cycle in which algae cells grown in an array of photo bioreactors are harvested and combusted in a combustion chamber to produce hot flue gases for cell drying. The heat combustion energy in this drying cycle is much higher than the energy required for drying the excess of algae cells and for the drying of the cells produced in the drying cycle. The combustion products in the flue gas produced by the drying desalination cycle is collected and recycled in the photo bioreactors for an additional cycle of harvesting, drying and combustion of algae cells. Thus, a third cycle is produced—the drying cycle, which provides all or almost all the energy for the algae cells drying. In this cycle, like in the other cycles, the source of energy is the sunlight which is converted to chemical energy by the algae cells.

The water which is evaporated from the wet algae cells during the drying stage is condensed back to liquid water while the flue gases are cooled to the growth temperature before entering the photo bioreactors. Consequently, large amounts of desalinated water are produced in the system. Per each gram of quicklime/cement, about 7 grams of desalinated water are produced by this system or 7-8 cubic meter are produced per each ton of cement.

The desalinated water can be used for other purposes (agriculture, etc.), while an equivalent amount of sea water is added to the photo bioreactors instead the desalinated water. In addition to the cement, ammonia and a huge excess of chemical energy (fuel) and by the same amount of sunlight energy a huge amount of desalinated water is also produced by the system.

Recycling of the combustion products: ($CO_2$ and Oxidized Nitrogen Compounds):
The recycling is performed in two stages. At the first stage, the combustion products are recycled directly by the algae cells from the gaseous phase above the cells suspension in the photo bioreactors to which the flue gases flow. At the second stage, the flue gases which leave the photo bioreactors with a very low concentration of combustion products react with the ammonia which flows in the opposite direction to the photo bioreactors as a source of nitrogen. The products of this reaction (ammonium nitrate, nitrite and ammonium bicarbonate) flow with the ammonia solution to the photo bioreactors and are also used as nitrogen source.

Additional Cycles:
The excess of cells produced by the basic core can be used as a source of combustion energy for other energy requiring plants, such as power plants, glass industry, etc. The flue gases produced in this plant are not released to the atmosphere but are also recycled in an additional array of photo bioreactors. Thus, a network of integrated cycles of various plants can be established which produces various products. Since the recycling of the flue gases released from the combustion chambers of the additional plants yields an amount of new algae cells which is equal or close to the amount of the combusted algae cells, such systems accumulate energy in the form of algae cells which increases continuously. The calculations suggest that the energy can increase in two ways: arithmetic progression or in geometrical progression, depending on two alternatives of the system arrangement:

1. If the rate of limestone firing in the system remains constant, then the energy accumulates in arithmetic progression.
2. If all or part of the excess of algae cells is used to increase the rate of limestone firing, then the energy accumulates in geometrical progression.

Theoretically this energy accumulation is endless. Practically, at a certain stage—this process of "energy inflation" has to be stopped by directing the excess of the algae cells or the excess of $CO_2$ produced in the system for other purposes. The excess of algae cells can be used as food, food additives, fertilizers, etc. The excess of $CO_2$ can be used for many industrial and commercial such as gazing drinks, welding devices, etc.

The present invention provides systems and methods for energy production. The method comprises the stages: (i) sustaining and regulating an algae culture in an array of at least one photo bioreactor, (ii) introducing $CO_2$ and nitrogen oxides from the combustion chamber of at least one kiln which is arranged for burning limestone and dolomite into clinker, (iii) harvesting algae from the bioreactors, (iv) producing energy in the form of the biomass of harvested algae. The system comprises at least one kiln for burning limestone and dolomite into clinker, at least one photo bioreactor for growing algae; pipeworks for feeding $CO_2$ and nitrogen oxides from the combustion chamber of a kiln to photo bioreactors; and pipeworks for feeding $CO_2$ released from burning limestone and dolomite to the array of photo bioreactors, at least one harvester for taking algae out of the photo bioreactors, an array of at least one cell dry and means for producing energy in the form of biomass of the algae taken out of the photo bioreactors. In some embodiments of the system, $CO_2$ from the kiln is used to intensify the growth of the algae in the photo bioreactors. A large excess of algae is produced by this synergetic arrangement, and this access can be used for electric energy production, water desalination and additional energy consuming processes.

According to some embodiments, the invention is a synergistic assembly of concerted closed cyclic processes for production of: energy, fuel, cement/quicklime, desalinated water and ammonia. Some of the devices produce energy (fuel) and some of them consume energy and the products of part of the cycles are the raw materials for other cycles in the system. The system comprises of: cement/quicklime production plant, electric energy production plant, water desalination plant, ammonia production plant, several bioreactors and additional energy consuming plants.

a) The energy supplied to these plants is sunlight energy converted to chemical combustion energy by algae cells grown in the photo bio reactors b) The plants of the system are fueled with dried or pyrolized algae cells produced in the photo bio reactors.

c) The $CO_2$, nitrogen oxides and other waste products produced by combustion in the system, and the $CO_2$ released during clinker/quicklime production, are sequestrated and recycled in the photo bioreactors for additional cycles of fuel production. No $CO_2$ releasing to the atmosphere and no air pollution.

d) The system is arranged in such a way that the amounts of carbon, nitrogen and other precursors for cell growth are steadily self-increasing by positive feedback. Consequently, the rate by which the system produces fuel is much higher (about 3.44 fold) than the rate by which the system consumes fuel. Thus, an excess of sun energy converted to chemical combustion energy (algae cells) is accumulated in the system by an accelerated rate.

e) In one possible arrangement, when the rate of limestone firing does not change, excess of energy produced by the system is accumulated by an arithmetic progression. In a second possible arrangement, when part of the excess is used to increase the rate of limestone firing, the excess is accumulated by geometrical progression. The amount of energy that can be supplied by this method is theoretically unlimited as long as there is enough area for algae cell growth.

f) The system supplies for itself all the energy required for its operation. The calculations have taken into account possible energy leakage in the system and a huge energy excess produced by this method is the net amount of energy that the system supply.

The operational energy of the system is supplied by additional cyclic electric energy production device fueled by algae from the photo bioreactors array, as was described above (U.S. Pat. No. 6,477,841 and EP0561436B1).

BRIEF DESCRIPTION OF THE DRAWINGS

The subject matter regarded as the invention will become more clearly understood in light of the ensuing description of embodiments herein, given by way of example and for purposes of illustrative discussion of the present invention only, with reference to the accompanying drawings (Figures, or simply "FIGS."), wherein.

DETAILED DESCRIPTIONS OF SOME EMBODIMENTS OF THE INVENTION

The present invention includes a system and method for energy production utilizing $CO_2$ emitted from burning limestone and dolomite to intensify the growth of algae in photo bioreactors. The algae biomass is then utilized to generate energy.

The term "Limestone" as used herein in this application comprises calcite, dolomite and a combination thereof.

Figure 1:
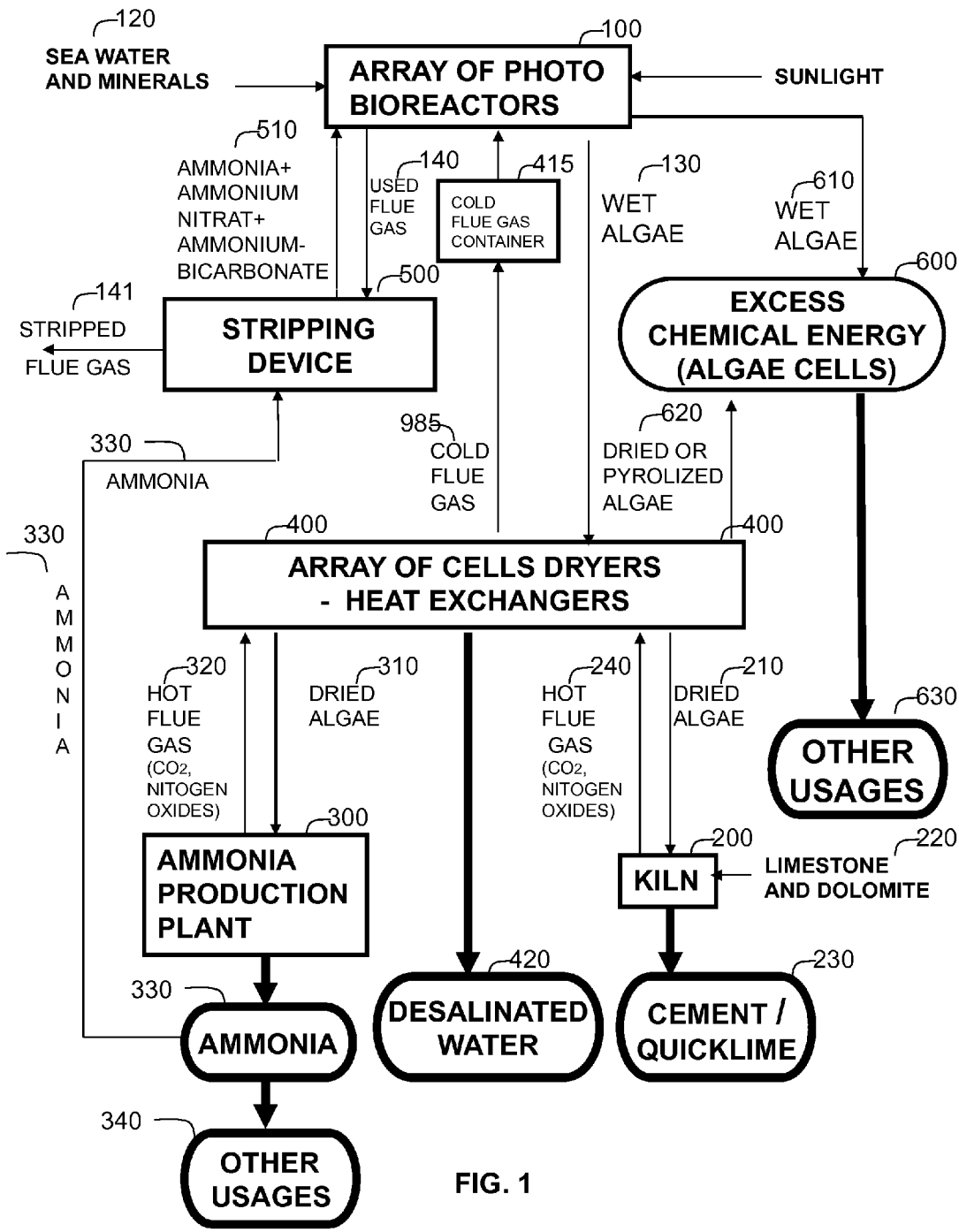
FIG. 1 is a block diagram illustrating the synergistic integration of the three cycles which are the core of the system and the devices which are geared together to one cyclic system which supplies cement/quicklime, excess of fuel as dried or pyrolized algae cells, desalinated water and ammonia by sunlight energy mediated by algae cells.
Figure 1A:
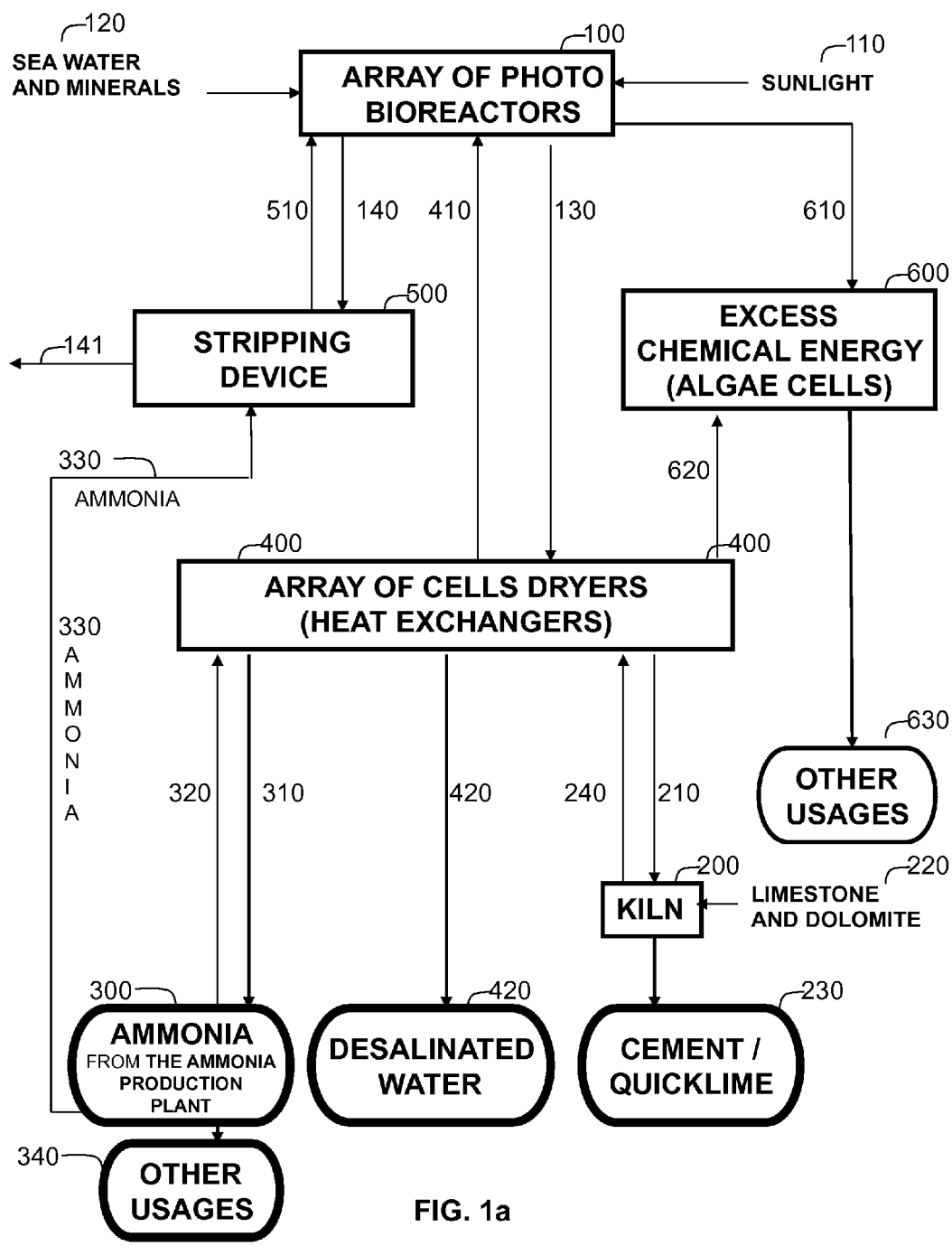
FIG. 1a is the same but without verbal tags, only numbers.

FIG. 1 is a block diagram illustrating the synergistic integration of all the three cycles and the devices which are geared together to one cyclic system which supplies cement/quicklime, excess of fuel as dried or pyrolized algae cells, ammonia and desalinated water by sunlight energy mediated by algae cells. Algae cells are grown in an array of photo bioreactors 100 supplied with sea water and minerals 120 and sunlight 110. The cells are harvested and the wet algae cells 130 are dried in an array of cells driers 400 which are also heat exchangers to cool hot gases 240 and 320. Part of the dried cells 210 serves as fuel in a kiln 200 for limestone and dolomite 220 firing. Another part of the dried cells 310 serve as fuel for ammonia production plant 300. In the kiln 200 limestone and dolomite 220 are fired to produce cement/quicklime 230. The hot flue gases 240 released from the kiln 200 are cooled in the array of the cells dryers 400 and so are the hot flue gases 320 which are emitted from the ammonia plant 300. The cold flue gases 410 from the cells dryers array 400 are returned to the array of photo bioreactors 100 to recycle the combustion products in the flue gas ($CO_2$ and NOx compounds) in order to produce additional cycles of algae cells. The amount of $CO_2$ released from the limestone 220 is about 2.44 fold higher than the amount of $CO_2$ produced by the algae cells combustion during limestone firing in the kiln 200. Therefore, an excess of $CO_2$ enters to the photo bioreactors from the limestone firing kilns. Therefore, an additional amount of nitrogen source has to be supplied to the photo bioreactors in order to recycle the additional amount of $CO_2$ as additional amount of algae cells. This nitrogen is supplied as ammonia 330 produced by the ammonia plant 300 fueled by algae cells 310. Remnants of $CO_2$ and NOx compounds in the used flue gas 140 which leaves the photo bioreactors array 100 are stripped by interaction with ammonia solution in a sequestration device 500 to produce ammonium nitrate and ammonium, bicarbonate 510 that can be also used as a nitrogen and carbon source in the photo bioreactors 100. The hot flue gases 240 and 320 serve as a source of energy to dry the wet algae cells 130 in the heat exchangers 400. The evaporated water from the cells is condensed when the flue gases 410 are cold enough before entering the photo bioreactors 100. A significant amount of desalinated water 420 is condensed and accumulates as desalinated water 420 which is one of the products of the system. Simultaneously, a new amount of sea water and minerals 120 are supplied to the photo bioreactors 100 in the same rate by which the desalinated water is supplied by the system. A huge amount of sunlight energy is converted to chemical energy and is accumulated in the system as dried or pyrolized cells 620 by a positive feedback mechanism and the yield of the system progressively increase. If the rate of limestone firing is not increased by this excess of energy—the excess of energy is accumulated in an arithmetic progression. If at least part of this excess is used to increase the rate of limestone firing—the energy accumulates in a geometrical progression. At a certain stage this increasing of the yield of the system 600 has to be stopped, and the excess of the energy has to be directed to other usages 630 by attaching to the system other energy requiring plants such as electric power plant, glass plants, metallurgical plants, etc. Part of the excess can be supplied as wet cells 610 for other usages 630 such as food additives, animals feeding, etc.

The Cement/Quicklime Cycle:

The rise in the concentration of $CO_2$ in the atmosphere indicates that the rate with which the biosphere assimilated $CO_2$ as biological carbon compounds is slower than the rate with which $CO_2$ is released by fuel consumption. This low productivity of the biosphere is the result of the low $CO_2$ concentration in the atmosphere and an adaptation of the existing ecological system to this low concentration.

One way to meet the requirements for carbon compounds is to establish a new artificial ecological system with higher productivity. This ecological system may be based on fast growing photosynthetic organisms and high concentration of $CO_2$ that can support higher growth rate. There is only one source of enough $CO_2$ for this purpose and that is calcite ($CaCO_3$) and dolomite ($MgCO_3$).

Almost all of the $CO_2$ on the surface of the world had been deposited as limestone and dolomite. The carbon in the limestone is not utilizable by the cells due to the low solubility of limestone and the negative free energy of the reaction between calcium and bicarbonate ions. Limestone is an endless resource of carbon for useful energy production. Fortunately the energy required to release the $CO_2$ from limestone is not too high, and the direction of the process can be reversed by the sunlight energy captured by the photosynthetic cells. The by product and by benefit of this process is quicklime and cement, which are produced by sunlight energy (mediated by cells without any cost for energy, and are highly required products anyhow).

According to some embodiments of the invention, the process is cyclic, continuous, closed to the carbon and nitrogen sources of the system ($CO_2$) and nitrogen source (ammonia and nitrogen oxides) with high product yield and a very high yield of light energy converted to chemical energy. Some of the advantages of the system are:

1. Cement and quicklime production has been one of the most energy intensive industries in the world (about 40-50% of the production cost). In this system the energy is supplied by the sun.
2. Cement and quicklime production are very heavy air polluting industries by $CO_2$—About 9% of the total $CO_2$ emitted yearly to the atmosphere. In this system all or almost all of this $CO_2$ is sequestrated and used to grow continuously additional cycles of micro algae cells.

Additional advantages of the cement cycle system are:
The materials are recycled ($CO_2$, sea water and nitrogenous compounds);
Cheap equipment and materials;
Cheap operation cost;
High yield of algae and therefore higher product yield;
Self supplying energy and nutrients;
Mass production.

According to some embodiments of the invention, most of the heat energy released during cell burning is produced by 2 reactions: Oxidation of hydrogen atoms to water, in which $\Delta H°=121$ KJ/mol Hydrogen atoms. 100 g of cells contain by mass about 8 g of hydrogen (8%). By burning 100 g of cells the heat energy released by hydrogen oxidation is about 121 KJ/g hydrogen·8 g=968 KJ, or about 9.68 KJ/g hydrogen. The energy ($\Delta H°f$) released during carbon oxidation to $CO_2$ is about 394 KJ/mol. The atomic mass of carbon is 12 g/mol. By dividing the molar energy released by burning of carbon by its atomic mass, the value of the heat energy released by burning 1 g of carbon is 32.8 KJ/g. About 50% of the cell mass is carbon. When burning 100 g of cells, the heat energy released from carbon oxidation is 50 g Carbon·32.8 KJ/g=1642 KJ, or about 16.42 KJ/g cells. Hydrogen and carbon contribute about 55-60% of the dried cell mass, and by burning them the heat energy produced is about (16.42+9.68) KJ/g cells=26.1 KJ/g cells. Taking into account oxidation of other elements contained in the cell—the heat energy produced is about 25 KJ/g cells. Algae cells are thus comparable to anthracite coal with 23 KJ/g. According to various reports, the combustion energy of algae cells varies in the range of 18-30 KJ/gram/ cells. Therefore, for the following calculation below, it is assumed that the combustion energy of the cells is 25 KJ/gram/cells.

According to some embodiments of the invention, the system and method utilize cheap and non-polluting quicklime and cement (CaO) production. The proposed invention includes energy production by sunlight energy with microalgae cells. Calcium oxide is usually made by the thermal decomposition of materials such as limestone, that contain calcium bicarbonate ($CaCO_3$); mineral, name calcite, according to the equation $CaCO_3+Heat \rightarrow CO_2+CaO$. When the temperature is between 800-1200 Degrees Celsius, the product is quicklime known also as burnt lime. At 1400 Celsius Degrees the product is clinker. The main operational cost of quicklime and cement production is the energy (about 40-50%). The raw material of cement production (Lime Stone) is very cheap, only a few percents of the overall operational costs. The kiln is fueled with dry micro algae cells.

According to some embodiments of the invention, the proposed system is cyclic and closed for the carbon source. All $CO_2$ released by burning the micro algae cells and during calcium oxide production is collected and flowed into the photo bioreactors to enable additional cycles of cell growth. Limestone (calcite and dolomite) is an excellent source of $CO_2$ for photosynthesis. During CaO production a huge amount of $CO_2$ is released from the limestone. 1 mol of $CaCO_3$ decompose to 1 mol of CaO (M=56 g/mol) and 1 mol of $CO_2$ (M=44 g/mol). Each ton of limestone decomposes to about half ton of quicklime and about half tone of $CO_2$.

According to some embodiments of the invention, and according to various references, the energy required to produce 1 ton CaO or 1 ton cement is about 4,000-4,600 MJ, or the energy required to produce 1 gram of CaO is about 4.6 KJ/g. The molecular mass of CaO is (40+16) g/mol=56 g/mol. The energy required to produce 1 mol of CaO is: 4.6 KJ/g CaO·56 g/mol=257.6 KJ/mol CaO. Since by burning 1 gram of cells, the amount of heat energy produced is about 26 KJ/g cell, then in order to produce 1 mol of CaO the amount of cells that have to be burned is 257.6 KJ/26 KJ/g cells=9.9 g cells. Assuming that the carbon content of the cells is 50% (4.93 g carbon), by burning 9.9 g cells, the amount of $CO_2$ released is:

$$4.93 \text{ g carbon}/12 \text{ g carbon/mol}=0.41 \text{ mol } CO_2.$$

The amount of $CO_2$ emitted from the limestone is much higher than the amount of $CO_2$ that was produced by burning cells to release this $CO_2$ from the limestone. Approximately 2.44 fold: 1 mol $CO_2$ from limestone/0.41 mol $CO_2$ from cells=2.44.

By supplying this amount of $CO_2$ (released from limestone) to additional photo bioreactors combined with the system, an additional amount of new cells is produced. This amount of the new cells is greater then the amount of the cells that have been burnt to release the $CO_2$ from the limestone by a factor of 2.44 fold. Taking into account that the $CO_2$ in the flue gas is completely (or almost completely) recycled, the amount of the new cells is higher by a factor of about 3.44 fold compared to the original amount of burnt cells. At the next stage, the amount of CaO and new cells also increases by a factor of 3.44 and so on.

Figure 2:
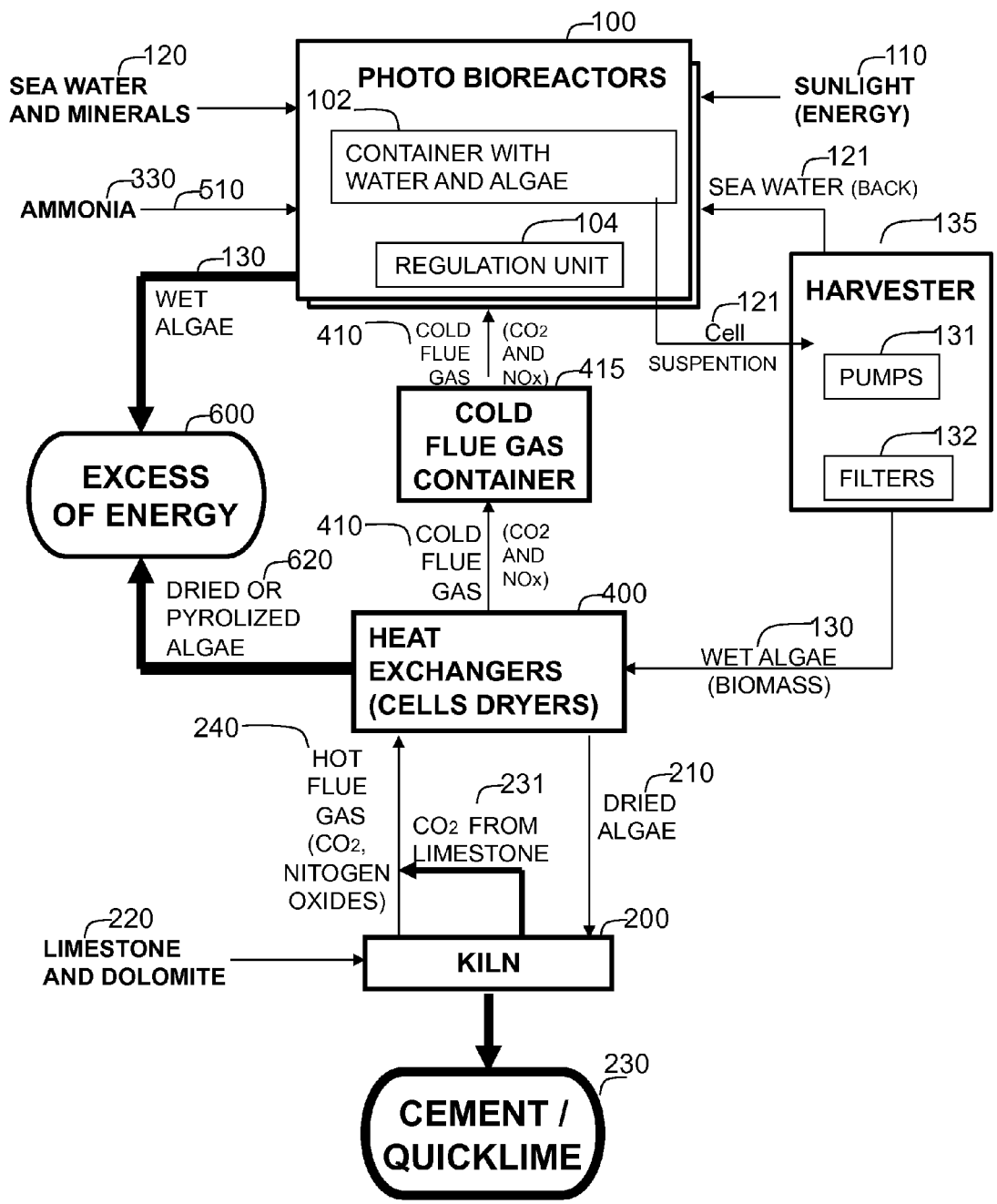
FIG. 2 is a block diagram illustrating a system for quicklime/cement and energy production, according to some embodiments of the invention.

FIG. 2 is a block diagram illustrating a system for quicklime/cement and energy production, according to some embodiments of the invention. The system comprises at least one kiln 200 for burning limestone and dolomite 220 into cement/quicklime 230. Kiln 200 is heated with energy (dried or pyrolized algae cells as fuel 210) and burning limestone and dolomite 220 produces large amounts of $CO_2$ 231. The system further comprises at least one photo bioreactor 100 for growing algae, comprising a container 102 with water and algae and a regulation unit 104. Photo bioreactors 100 receive sea water and minerals 120 and sunlight 110. The photo bioreactors 100 also receive $CO_2$ 231 released from the limestone and $CO_2$ and NOx compounds 240+410 which are contained in the flue gases produced in the combustion chamber of the kilns 200 during algae combustion and these are regulated by regulation unit 104.

Additional nitrogen source is ammonia 330 which is produced in the ammonia plant 300 of this system and additional nitrogen compounds 510 which are produced in the stripping device 500 (not shown in this figure). This nitrogen sources enable the production of the excess of algae cells 600 produced by the excess of $CO_2$ 231 released from the kilns 200.

The system is closed and cyclic. The gases and the liquid materials in the system flow through a net of pipe works connecting the various devices of the system as well as further possible attached plans. The $CO_2$ 231 released from the limestone 220 as well as the ammonia 330 and the nitrogen compounds 510 intensify the growth of the algae in photo bioreactors 100, while the $CO_2$ and NOx compounds produced by algae combustion enable the production of algae cells in the same rate by which they are combusted for limestone firing. The system further comprises a harvester 135 for taking algae suspensions 125 out of photo bioreactors 100 by pumps 131. The algae are harvested by filters 132 and the wet algae cells 130 are conveyed for drying in the heat exchangers 400. The water remained after the filtration 121 is fed back to the photo bioreactors 100.

Figure 12:
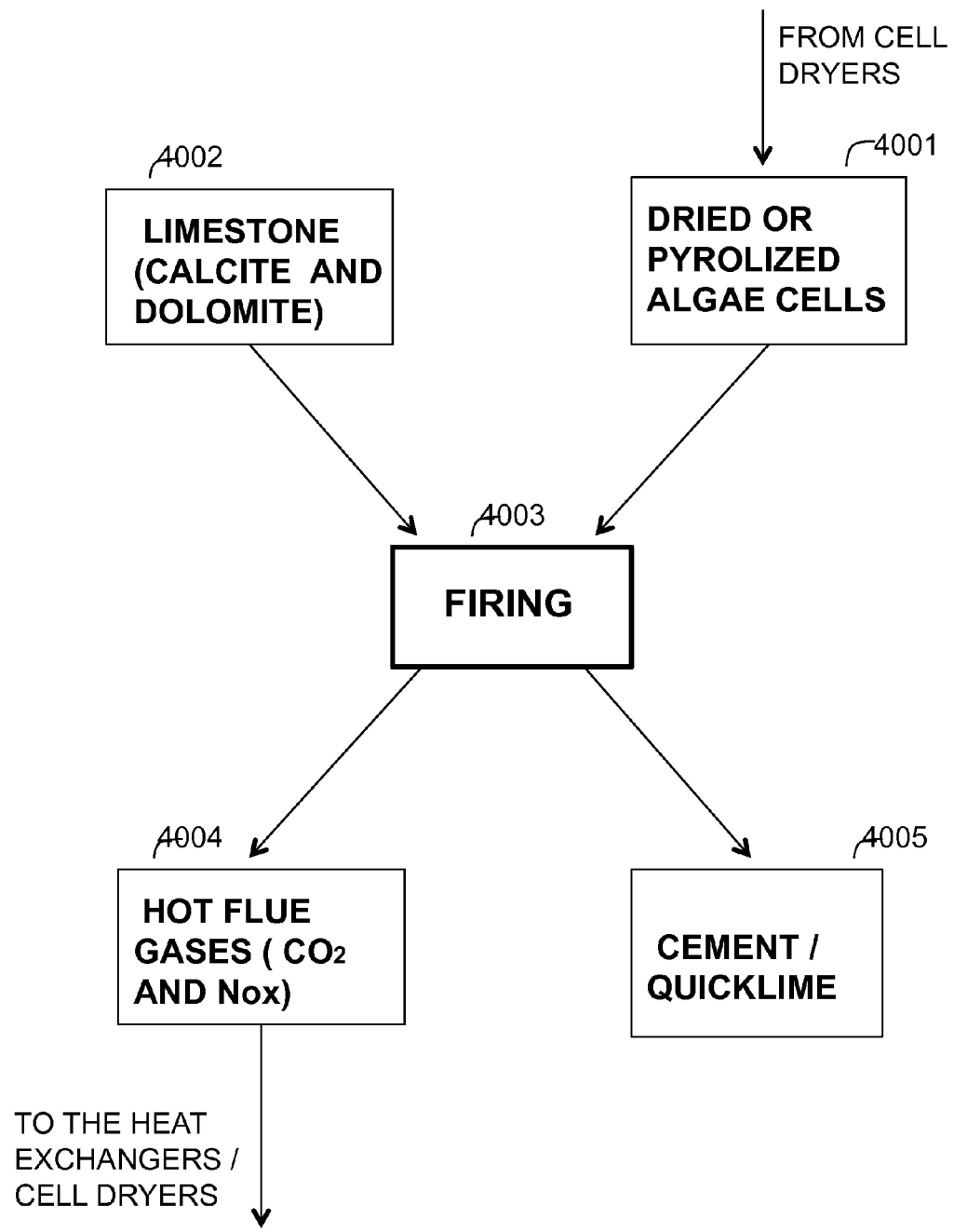
FIG. 12 is a flowchart illustrating a method of cement and quicklime production according to some embodiments of the invention.

FIG. 12 is a flowchart illustrating a method of cement and quicklime production according to some embodiments of the invention. The method comprises the stages:

Providing limestone to at least one firing kiln (stage 4001);
Providing dried or pyrolized algae to fuel the kilns from the heat exchangers/cell driers (stage 4002);
Firing limestone by combusted algae cells (stage 4003).
Providing hot flue gases from the kilns to the heat exchangers/cell driers (stage 4004).
Collect cement and quicklime (stage 4005).

A large excess of algae is produced by this synergetic arrangement.

According to some embodiments of the invention, substantially all $CO_2$ released by burning limestone and dolomite into clinker in kiln 200 is introduced into photo bioreactors 100. According to some embodiments of the invention, at least one analyzer may be connected to a control system, and arranged to keep the $CO_2$ and nitrogenous compounds (nitrogen sources) concentration in photo bioreactors 100 at an optimal level (e.g. 0.1% concentration of $CO_2$ in the gaseous phase of the photo bioreactors 100). The control system 104 also regulates the harvesting of the algae cells to the appropriate rate according to their consumption in the various plants of the system. The algae concentration in the cells suspensions 102 are held fixed and the rate of harvesting is equal to their growth rate.

There are two possible kinetics by which the algae cells excess is increasing (the inflation process) with various combinations and various proportions between them:

a. $CO_2$ amplification. All or part of the new excess cells is used to release an additional amount of $CO_2$ by increasing the amount of limestone firing. The result is a successive cascade of amplifications. With this arrangement, the energy produced by the system is accumulated by a geometrical progression. If all of the excess is used to increase the rate of CaO production, the capacity of the system progresses geometrically with a factor of about 3.44. Even if only a part of the excess cells is used to increasing the amount of limestone firing, the capacity of the system still progresses geometrically with a factor smaller then 3.44 as long as the process is cyclic and the amount of $CO_2$ that remains in the system at a certain stage is greater than the amount of the previous one. This means that the amount of sunlight energy that is converted and accumulated by the cells as chemical energy is also increasing geometrically.

b. The rate of CaO production does not increase. All of the excess new cells (that are produced with the $CO_2$ released from limestone) are not used to increase CaO production. Taking into account that $CO_2$ in the flue gases of the additional consuming plants included in the system are also sequestrated, the amount of cells which accumulate in the system increases by an arithmetic progression with an increment of 2.44 g of new cells per every 1 g of cells consumed in the kilns.

Theoretically, this increasing process is endless and the amount of energy that the system can supply is unlimited. The only practical limitation is available areas on the globe. Obviously, at a certain stage this increasing process should be stopped by using the excess of produced new cells or the excess of $CO_2$ for additional applications.

There are two alternative usages to this increasing excess of biomass and energy:
a. Enlargement of the system by adding more and more energy consuming plants such as electric power plant, glass industries, etc. Practically, this enlargement must be stopped at a certain size.
b. Use of at least part of the new cells produced by the system, and at least part of the $CO_2$ released from limestone for other utilities such as:
  1) The excess of $CO_2$ can be supplied to additional Photo bioreactors in which other kind of micro algae cells (or other photosynthetic organisms) grow and produce other important products (food, Omega 3, Vitamin C, source of protein, food additives, animal feeding etc).
  2) Bio-diesel production.
  3) Chemical industries like ammonium bicarbonate, liquid and solid $CO_2$ production, rubber and plastics industry, pharmaceuticals and petroleum industry, silicone production etc.).
  4) Hydrogen ($H_2$) production (by electrolysis).

The Ammonia Cycle:
The nitrogen oxides produced during algae cells combustion can be up-taken by algae cells and recycled in the closed cyclic systems, but the amount of these nitrogen oxides enables the production of no more then 1 gram of new cells per each gram of consumed cells. Production of 3.44 grams of new cells per each gram of consumed cells requires additional amounts of nitrogen for production of the rest 2.44 grams of new cells. These additional amounts are supplied as ammonia ($NH_3$).

Cells contain about 14-15% Nitrogen by mass. Ammonia is produced by Haber-Bosch process at high temperature (400-500° c.) and high pressure (300-1000 at). Although the reaction between nitrogen and hydrogen is very exothermic ($\Delta Hf°=-94$ KJ/mol Ammonia) the activation energy is very high, and this is one of the most intensive energy consuming industrial processes. According to various references, the specific energy consumption of ammonia production varies between 40 KJ/g ammonia to 28 KJ/g ammonia. Taking an average value of 35 KJ/g ammonia, the energy consumed for production of 1 mol ammonia is about:

$$35 \text{ KJ/g ammonia} \cdot 17 \text{ g/mol ammonia} = 595 \text{ KJ/mol ammonia}.$$

100 g cells contain about 1 mol of Nitrogen (14-15% by mass, M=14 g/mol nitrogen).
Since Every Mol of Nitrogen in the Cells is Supplied by a Mol of Ammonia,
595×)/mol ammonia is the energy required to produce the ammonia for growth of 100 g cell. For production of 1 g cells the required amount of energy is: 5.95 m/g cells which is only 24% of the combustion energy of the cells (25-26 KJ/g cell). Hence, in order to produce 2.44 grams of new cells, 12% of this amount, which is 0.59 gram cells has to be combusted in the ammonia production plant.

Figure 3:
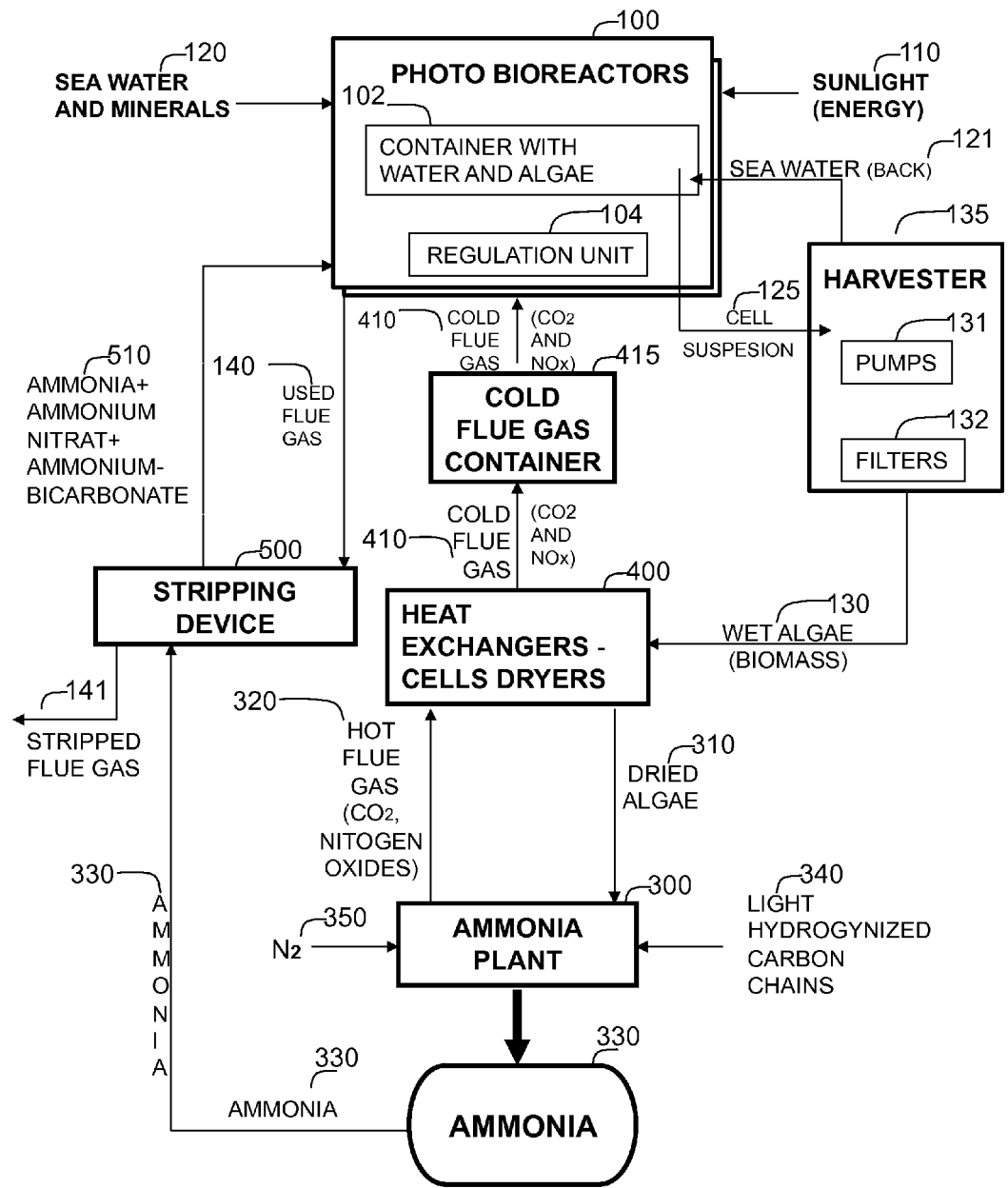
FIG. 3 is a block diagram illustrating the ammonia production cycle, according to some embodiments of the invention.
Figure 3A:
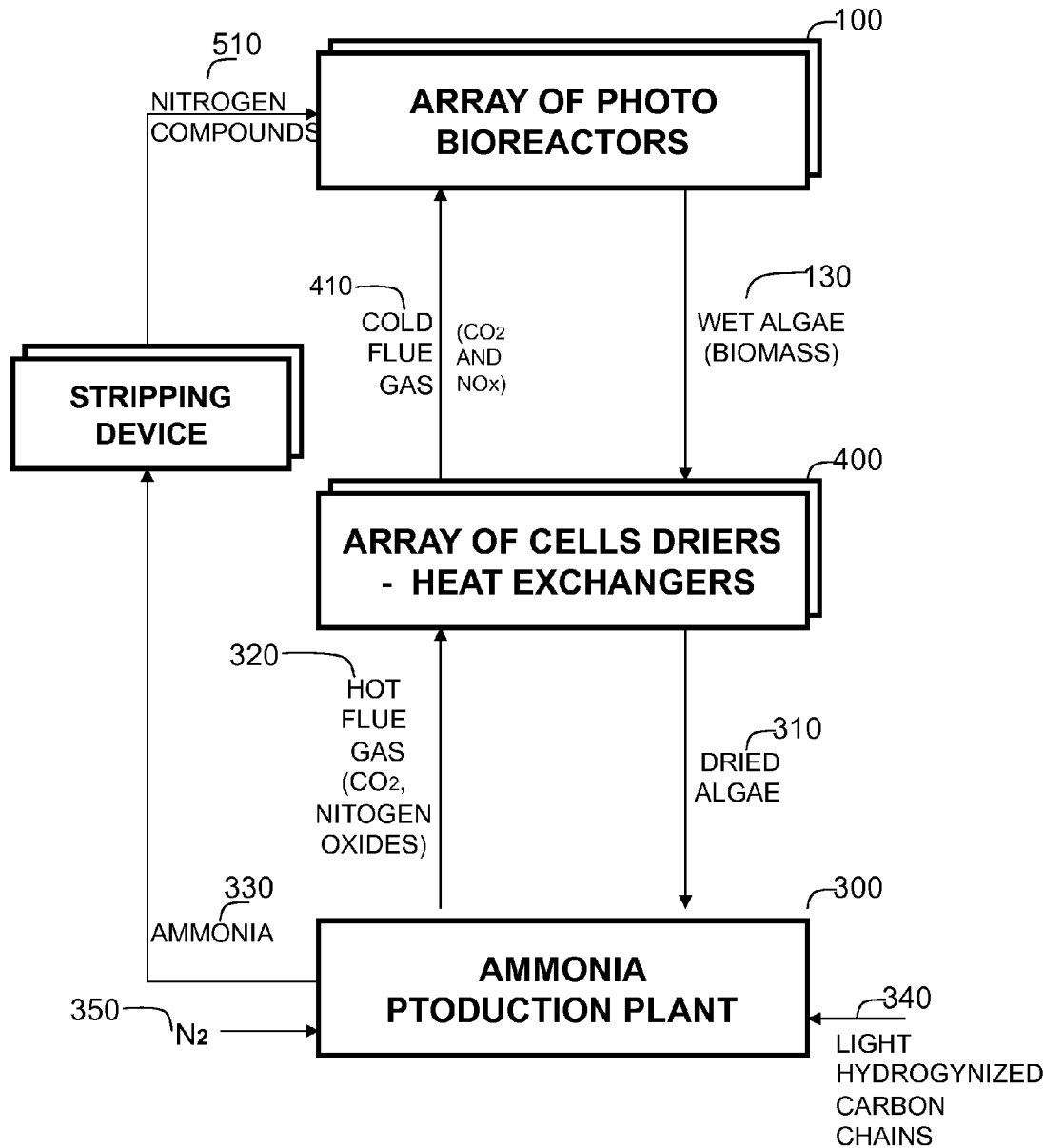
FIG. 3a is a simplified block diagram of the ammonia cycle, illustrating its main outlines.

FIG. 3 is a block diagram illustrating the ammonia production cycle. The ammonia production plant 300 is fueled by dried or pyrolized algae cells 310. The hot flue gas 320 produced in the ammonia plant is cooled in a cell drier-heat exchanger 400, and is used as source of $CO_2$ and nitrogen oxides for production of similar amount of new wet cells 130 in a photo bioreactors 100. These new cells are harvested 135, dried in the cell drier 400, and combusted in the ammonia production plant 300, as a source of energy. The ammonia 330 flows into the sequestration device 500 in opposite direction to the used flue gas 140 that leaves the photo bioreactors 100. Remnants of $CO_2$ and NOx compounds in the used flue gas 140 which leaves the photo bioreactors array are stripped by interaction with ammonia solution 330 in a sequestration device 500 to produce ammonium nitrate and ammonium bicarbonate. This mixture 510 serves as a nitrogen and carbon source in the photo bioreactors.

The input energy of 5.95 KJ/g cells for ammonia production is required for the photo bioreactors in which the excess of cells is produced (by the $CO_2$ emitted from limestone). Theoretically, if the fuel for ammonia production is supplied as algae cells, about 24% of the excess has to be allocated for ammonia production. Actually, this amount can be much smaller. The ammonia production plant 300 within such system is fueled by dried or pyrolized algae cells 310 and the flue gas 320 produced in the ammonia production plant 300 is recycled and used as source of $CO_2$ and nitrogen oxides for production of similar amount of new cells in the photo bioreactors array 100 connected to the plant. Thus, an additional ammonia production cycle can be created in which new cells are dried and combusted in the ammonia production plant as a source of energy. All, or almost all, of the cells used for ammonia production can be new cells produced by this cycle and only a small amount (if any) has to be allocated from the excess.

Figure 13:
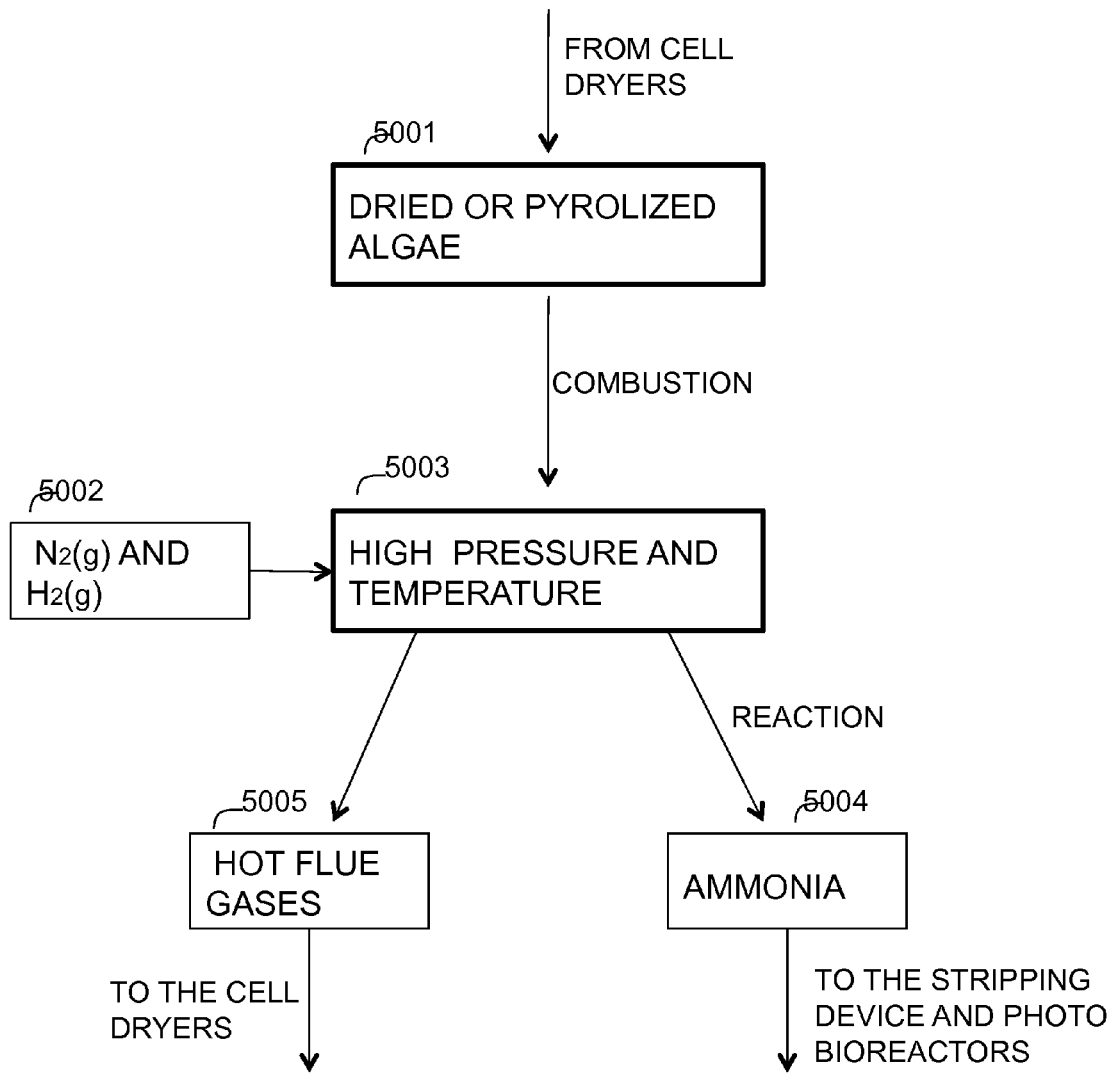
FIG. 13 is a flowchart illustrating a method of ammonia production according to some embodiments of the invention.

FIG. 13 is a flowchart illustrating a method of ammonia production according to some embodiments of the invention. The method comprises the stages:
  Providing dried or pyrolized algae to fuel the ammonia production from the heat exchangers/cell driers (stage 5001);
  Supplying atmospheric nitrogen (N2) and hydrogen source (stage 5002);
  Producing high pressure and temperature by combustion of the dried or pyrolized algae (stage 5003).
  Ammonia production (stage 5004).
  Providing aqueous ammonia solution from the ammonia production plant to the stripping device and to the photo bioreactors (stage 5005).
  Providing hot flue gases from the ammonia plant to the heat exchangers/cell driers (stage 5006).

Drying and Pyrolysis of Algae Cells and Water Desalination:
the specific evaporation energy of water ($\Delta Hev$) at 25° C. is 2.4 KJ/g water. More than 90% of the harvested cell's content is water, and water also exists among the cells. Hence, the specific evaporation energy of the cells is approximately similar to that of water, i.e. 2.4 KJ/g cells. Loss of heat energy to the surrounding has also been kept in mind (a loss of about 30% with good isolation), thus the actual evaporation energy of 3.1 Kj/g cells is a reasonable approximation. This amount of energy is about 12% of the heat energy content of the cells. In experiments with closed cycles it has been demonstrated that the heat energy in the flue gases is enough, or almost enough, to dry the harvested cells burnt in the cycle (for electric energy production, etc.). But in these experiments the amount of the dried new recycled cells was equal to the amount of the burnt cells. In the proposed system the amount of new cells is not equal but higher by 3.44 folds, compared to the original amount of burned cells for quicklime firing. Therefore, it is doubtful whether the energy in the flue gas produced during quicklime firing is enough for drying all the amount of the new produced cells.

Figure 4:
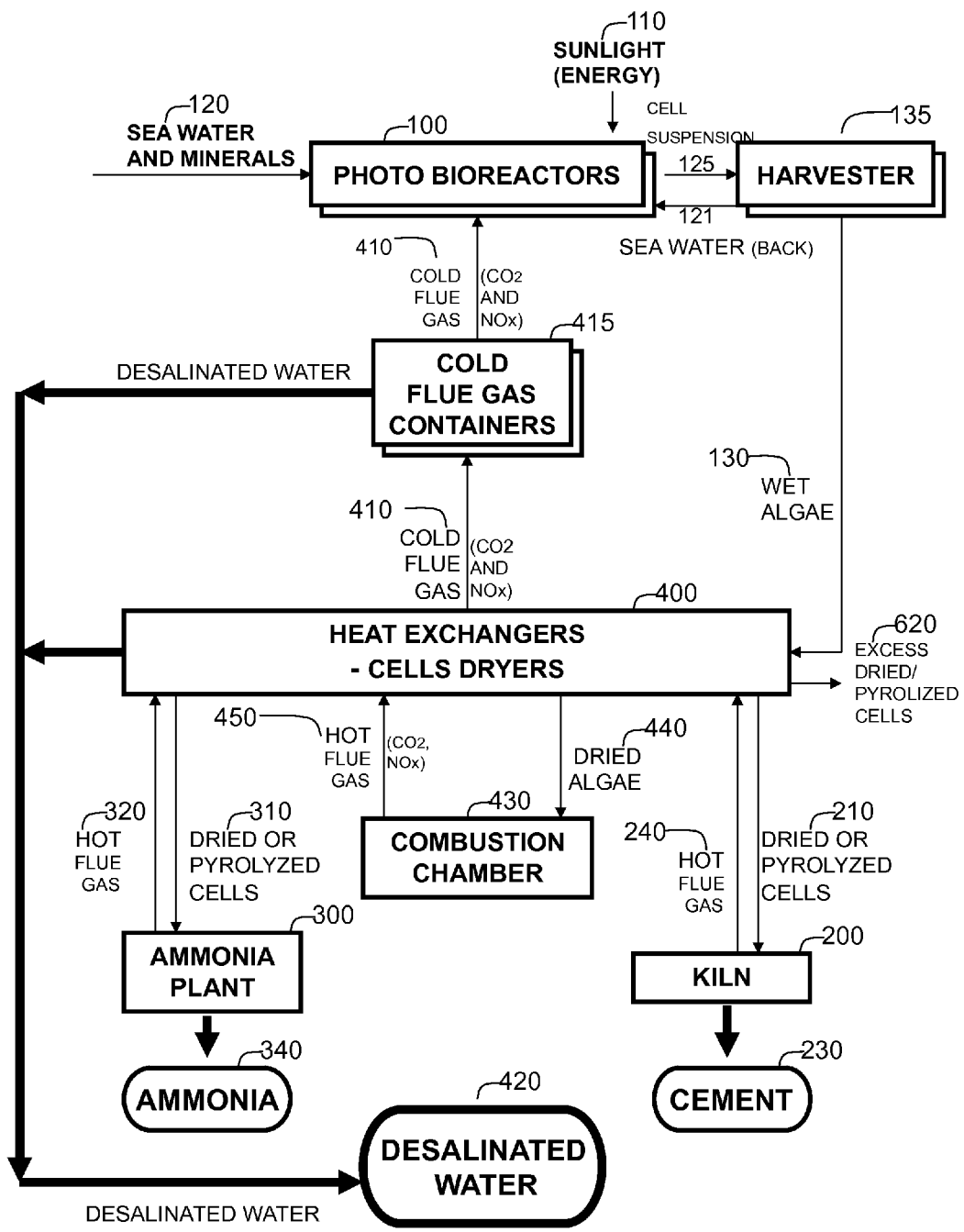
FIG. 4 is a block diagram of the drying process and water desalination, according to some embodiments of the invention.

FIG. 4 is a block diagram of the drying process and water desalination. Let's assume that the amount of heat energy required to dry the excess of algae cells is produced by burning a part of cells which are taken from the excess of the dried cells 620. This part 440 is taken from the heat exchangers—cells driers array 400 and combusted in a combustion chamber 430 which adds appropriate amount of hot flue gas 450 to the heat exchangers-cells driers array 400. Theoretically, this part is supposed to be 12% of the excess 620, but actually this part is expected to be much smaller (if any). The combustion products in the flue gas 450 produced by these burnt cells 440 are added to the flue gases 410 that flow to the photo bioreactor array 100 and are also recycled in the photo bioreactors array 100 which supplies cells to the drying devices 400 as is described by FIG. 4. The result is a closed drying cycle in which the energy for the drying process is sun energy 110, mediated by photosynthetic cells and most, or almost most, of the cells burnt in this cycle are produced by the cycle itself and are not taken from the excess. As can be seen from the above calculation, the system has enough energy to dry the cells it produces and still a substantial proportion of energy is left for additional purposes.

The conditions in the drying process (lack of oxygen, 500° c.) can be adjusted in such a way that all or part of the cells is pyrolized during drying. The system can produce a liquid fuel of pyrolized cells in addition to whole intact dried cells. This liquid fuel can be used by:

a. Additional devices which are not included in the system
b. Devices which are included in the system when liquid fuel is technologically preferred.

The flue gas 410 that leaves the cell driers array 400 contains a lot of water. This water is produced in the combustion chambers 430, in the limestone kiln 200, in the ammonia plant 300 and during evaporation from the wet cells 130 in the drying device 400. In order to flow the flue gases 240, 450 and 320 into the photo bioreactors 100 their temperature has to be lowered in the heat exchangers of the drying device 400 to the growth temperature of the algae cells 410. At this temperature, the water is condensed back again to the liquid state. This water accumulates in the heat exchanger 400 and in the storage of cold flue container 415. This is desalinated water 420 that may contain very small amounts of NOx compounds which are harmful to human beings and animals but can serve as a nitrogen source for plants. This water 420 can be returned to the photo bioreactors 100 together with the other combustion products, but a better option is to use it as desalinated water for other purposes, while same amount of sea water are added to the photo-bioreactors instead of the desalinated water. The NOx compounds can be absorbed by filters in order to use this water by human being and animals or to irrigate plants.

Figure 9:
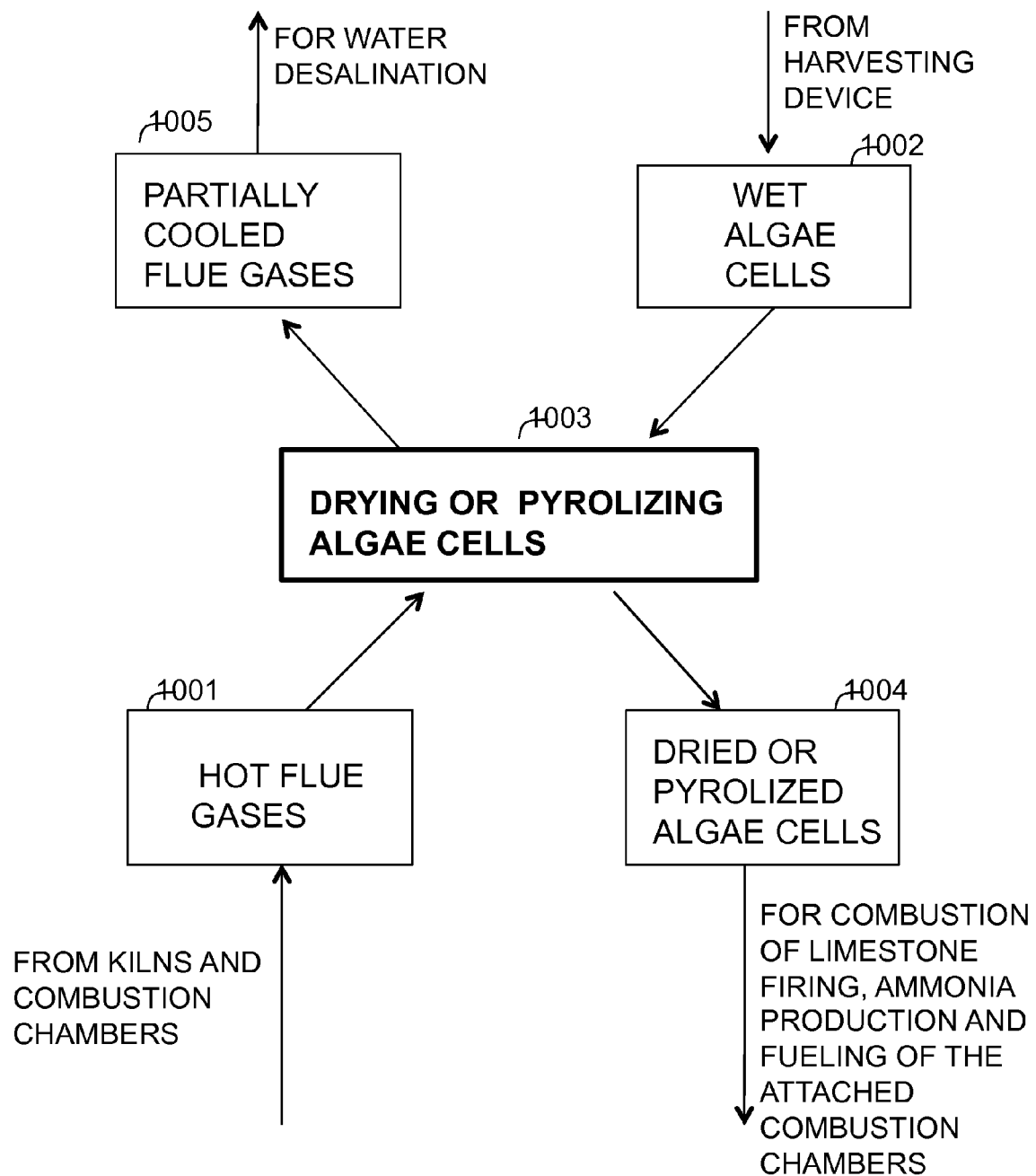
FIG. 9 is a flowchart illustrating a method of drying and pyrolizing algae, according to some embodiments of the invention.

FIG. 9 is a flowchart illustrating a method of drying and pyrolizing algae, according to some embodiments of the invention. The method comprises the stages:

Providing hot flue gases from kilns and combustion chambers to at least one heat exchanger (stage 1001);
Providing wet harvested algae cells to at least one heat exchanger (stage 1002);
Drying or pyrolizing the cell algae by the hot flue gases (stage 1003); and
Fueling the kilns and the combustion chambers by the dried or the pyrolized algae (stage 1004).
Supplying partially cooled flue gases saturated by water vapor for water desalination (stage 1005).

Figure 10:
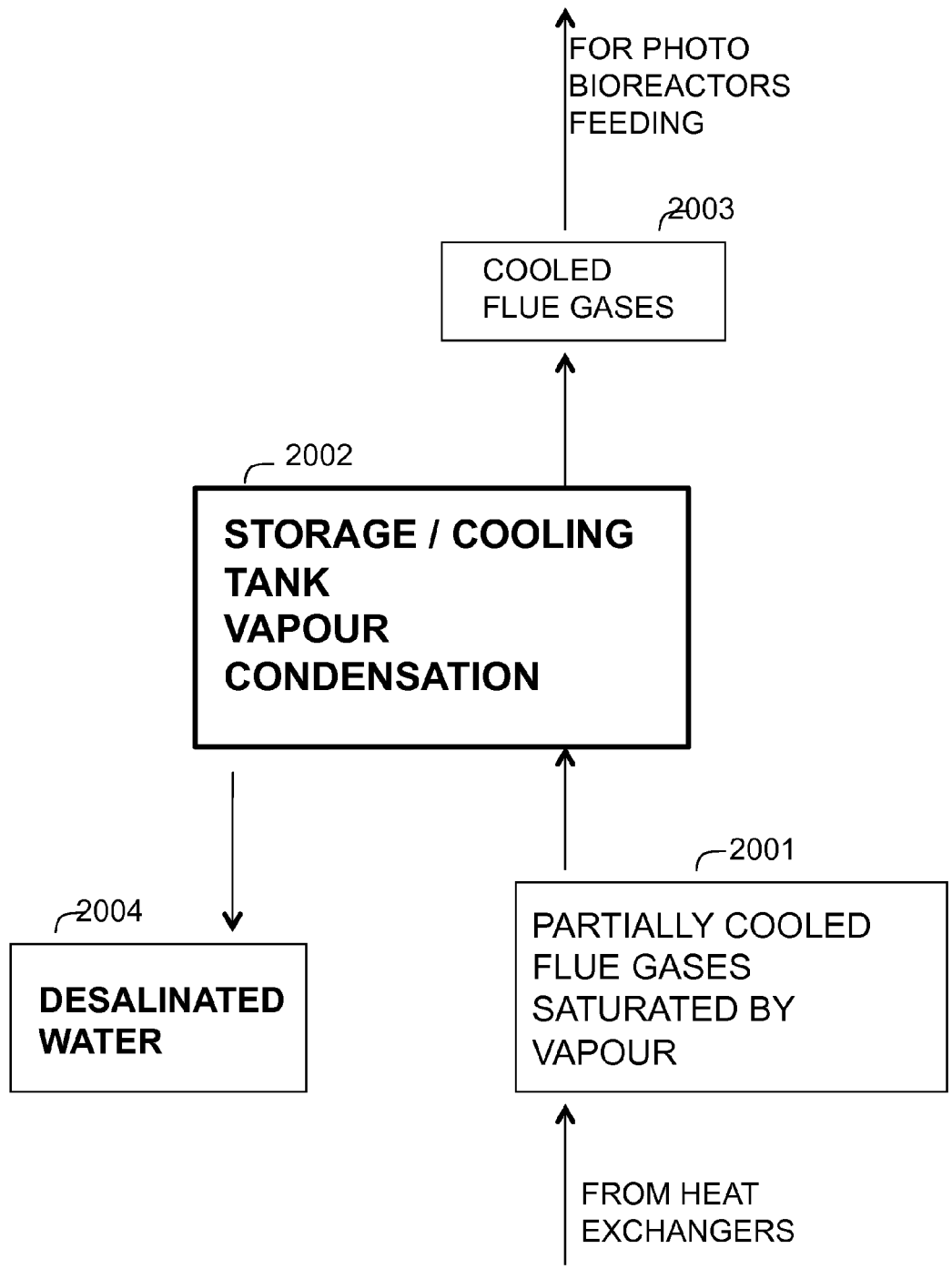
FIG. 10 is a flowchart illustrating a method of water desalination according to some embodiments of the invention.

FIG. 10 is a flowchart illustrating a method of water desalination according to some embodiments of the invention. The method comprises the stages:

Providing partially cooled hot flue gases saturated by water vapor from the heat exchangers/cell driers to at least one storage/cooling tank (stage 2001);
Vapor condensation (stage 2002);
Supplying cooled flue gases to the photo bioreactors (stage 2003); and
Collecting desalinated water from the bottom of the storage/cooling tank (stage 2004).

In large industrial scales, such systems can be a significant source of fresh water. More then 90% of the wet cell content is water, and there is also water among the cells. Hence, approximately 0.95 gram of desalinated water can be obtained from 1 gram of wet algae cells and approximately 9.5 gram of desalinated water can be obtained from 1 gram of dried algae cells. From each gram of dried cells which are aimed for limestone firing—3.44 gram of new dried cells are produced. Therefore, about 32 grams of desalinated water are produced by each cycle of the limestone firing process. An additional amount is added from the ammonia production cycle. Per each 3.44 grams of dried cells in the limestone cycle, 0.59 grams of dried cells are combusted in the ammonia cycle. Hence the ammonia cycle contributes about 5.6 grams of desalinated water per each cycle of the limestone firing process. To the amounts of desalinated water produced in the limestone cycle and the ammonia cycle, additional amounts are added from the drying cycle itself and from the combustion chambers in where the hydrogen in the dried cells is oxidized to water. Since per each gram of dried algae cells combusted for limestone firing about 5 grams of cement are produced, it can be concluded that per each gram of cement, about 7-8 grams of desalinated water are produced in addition to the surplus of cells excess and by the same amount of sunlight energy.

Figure 5:
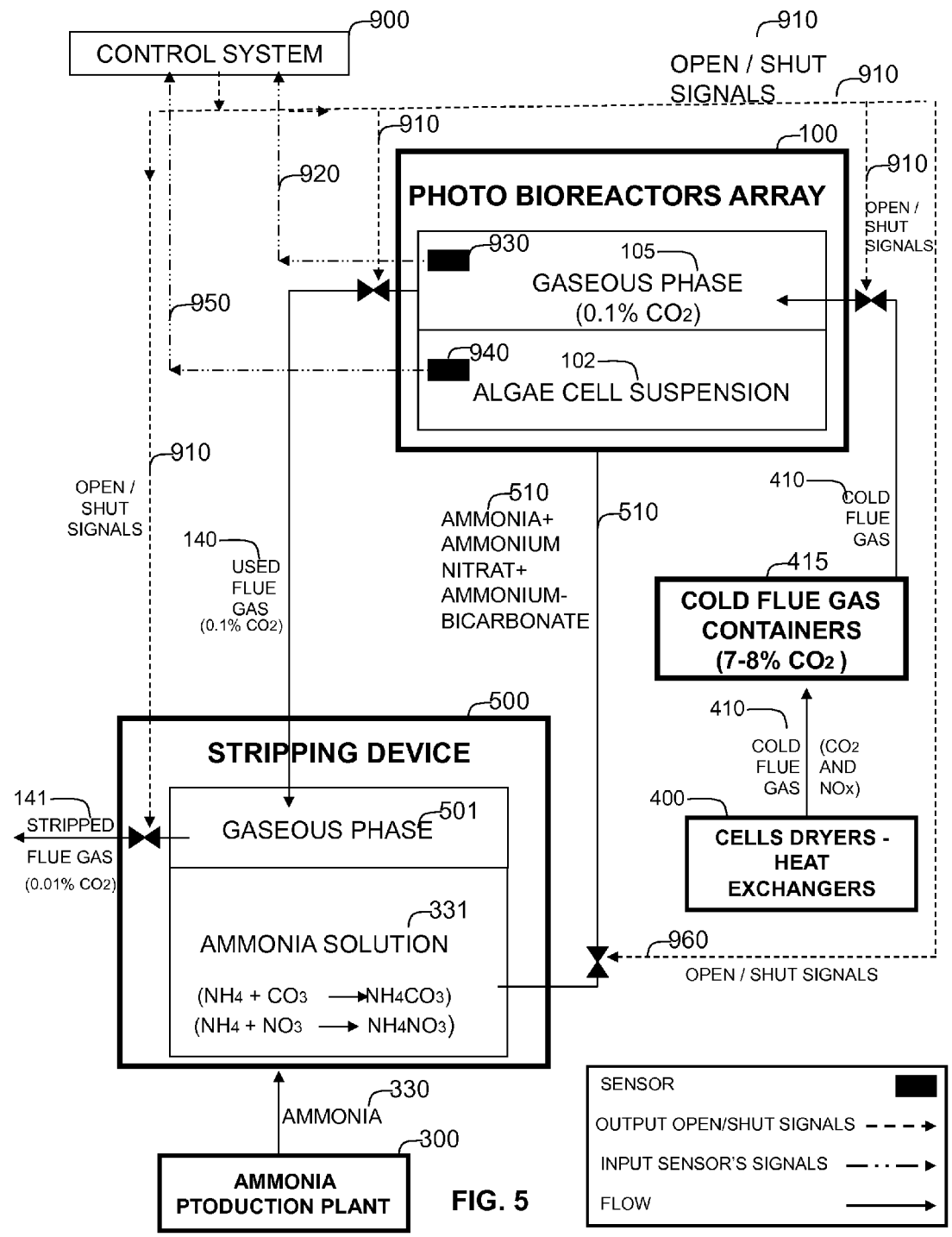
FIG. 5 is a block diagram illustrating the stages of the recycling process.

$CO_2$ and NOx Sequestration:

According to some embodiments of the invention, the method comprises recycling of the $CO_2$ and NOx compounds in the flue gas according to the following material balance calculation. FIG. 5 is a block diagram illustrating the stages of the recycling process. The concentration of $CO_2$ in the exhaust gas of engines or power plant varies between 3% when the fuel contains high hydrogen content (hydrocarbon) and 15% when the fuel is coal (close to 100% carbon). Since cells contain about 50% carbon, it is assumed that the cold exhaust gas of burnt cell 410 which enters to the gaseous phase 105 above the cells suspensions 102 contains an average value of 8-9% of $CO_2$. Hence, most of the volume of the exhaust gases is not $CO_2$ but other gasses. Since most of the volume of the flue gas is not $CO_2$ or NOx compounds, and the space in the photo bioreactor is limited, most of the exhaust gas must be released from the photo bioreactor with part of the $CO_2$ and NOx compounds in the exhaust gas, and cannot be completely recycled by the micro algae in the growth medium 102. The concentration of the $CO_2$ in the gaseous phase 105 is kept by controlled supply rate 900 of cold flue gas with 8-9% $CO_2$ concentration 410 from the flue gas containers 415, flow into the photo bioreactors 105. $CO_2$ sensors 930 continuously feed the control system with data 920 and the concentration of the $CO_2$ in the gaseous phase 105 is kept at about 0.1% by open/shut signals 910 from the control system. These open/shut signals regulate the valves which control: (1) The flow of the cold flue gas 410 into the photo bioreactors 105; (2) The flow of the used flue gas 140 from the gaseous phase of the photo bioreactors 105 to the stripping device 500; (3) The flow of the stripped flue gas 141 from the gaseous phase 501 of the stripping device to the atmosphere. This implies that the rate by which the $CO_2$ is supplied to the cells suspensions 102 by the cold flue gas 410 is equal to the rate by which the algae cells in the suspension assimilates the $CO_2$ from the gaseous phase 105. $CO_2$ concentration of about 0.1% is about 3 fold higher then the $CO_2$ concentration in the atmosphere. In such concentration, the growth rate of the algae cells is maximal or closed to the maximum. While cold flue gas 410 with 7-8% $CO_2$ concentration flows into the photo bioreactor, equal flow (same volume) of used flue gas 140 leaves the bio reactor, with $CO_2$ concentration of about 0.1%. This implies that most of the $CO_2$ in the flue gas (about 98.7%) is sequestrated directly by the growing cells. Similar proportions of the NOx compounds are also sequestrated directly by the cells.

The remained 0.1% $CO_2$ and the NOx compounds that leave the photo bioreactors with the used flue gas 140 are stripped in the stripping device 500. In this device, the gaseous phase 501 is in contact with the ammonia solution 331 that flows from the ammonia production plant 300 in opposite direction. The $CO_2$ in the used flue gas reacts with the ammonia ($NH_3$) to produce ammonium bicarbonate ($NH_4CO_3$). The nitrate ions react with the ammonia to produce ammonium nitrate ($NH_4NO_3$) Experiments show that more than 90% of the $CO_2$ react with the ammonia. Thus, the stripped flue gas 141 that is released to the atmosphere from the ammonia tank contains only about 0.01-0.02% $CO_2$, much less then the $CO_2$ concentration in the air (about 0.033%). The mixture of ammonia, ammonium nitrate and ammonium bicarbonate 510 is than supplied to the cells suspension 102 as a nitrogen source. Sensors 940 feed the control system with data about the ammonia concentration in the cells suspension 950 and the flow of the nitrogen to the cells suspension is controlled by open/shut signals 960 that control the flow of this mixture 510 to the cells suspension 102.

Figure 11:
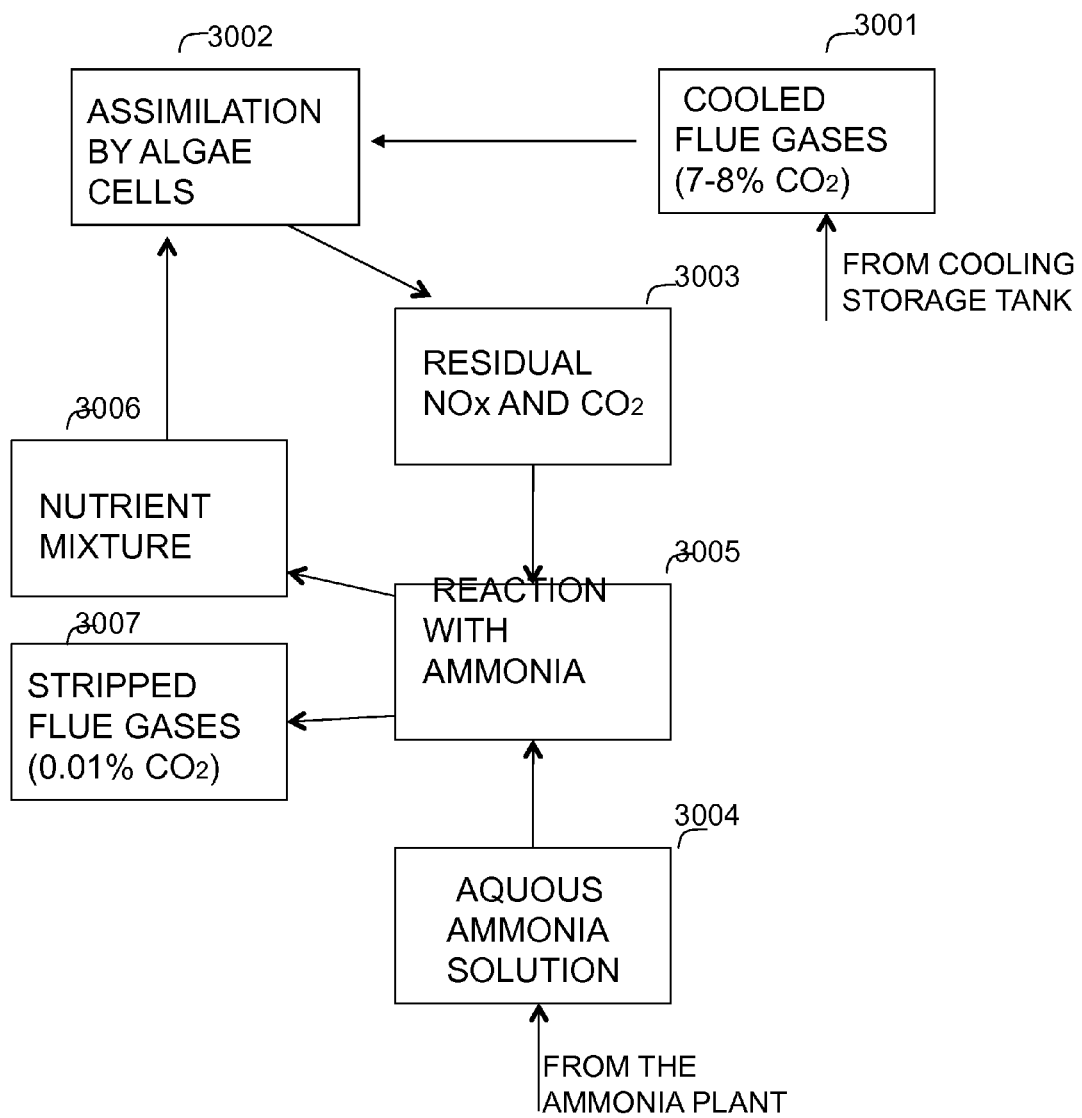
FIG. 11 is a flowchart illustrating a method of $CO_2$ and nitrogen oxides sequestration according to some embodiments of the invention.

FIG. 11 is a flowchart illustrating a method of $CO_2$ and nitrogen oxides sequestration according to some embodiments of the invention. The method comprises the stages:
- Providing cooled flue gases containing about 7-8% $CO_2$ from the storage/cooling tank to the photo bio reactors (stage 3001);
- Assimilation of dissolved $CO_2$ and nitrogen oxides by algae cells (stage 3002);
- Providing sequestrated flue gases with residual $CO_2$ and nitrogen oxides (about 0.1% $CO_2$) from the photo bio reactors to the stripping device (stage 3003).
- Providing aqueous ammonia solution from the ammonia production plant to the stripping device (stage 3004).
- Reacting of the residual $CO_2$ and nitrogen oxides with the aqueous ammonia solution (stage 3005).
- Providing the mixture of the aqueous ammonia solution and the reaction products from the stripping device to the photo bio reactors as an available source of nitrogen and carbon (stage 3006).
- Releasing stripped flue gases (about 0.01% $CO_2$) from the stripping device to the atmosphere (stage 3007).

Figure 6:
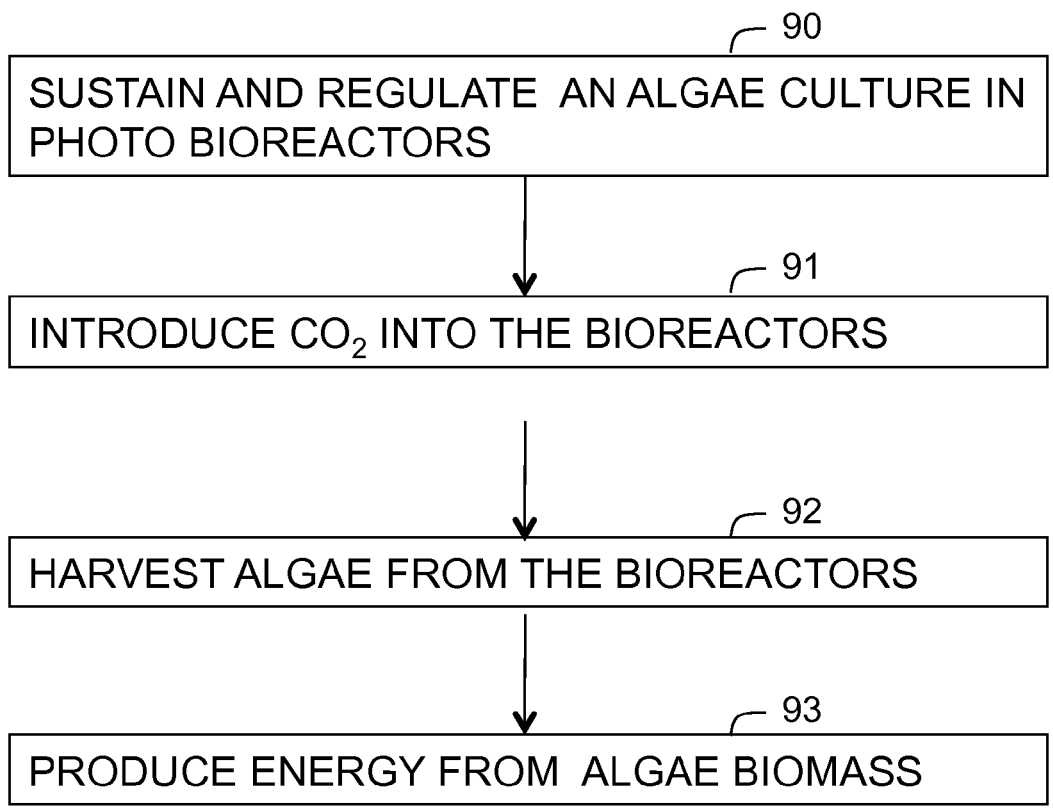
FIG. 6 is a flowchart illustrating a method of producing energy, according to some embodiments of the invention.

FIG. 6 is a flowchart illustrating a method of producing energy, according to some embodiments of the invention. The method comprises the stages:
- Sustaining and regulating an algae culture in one or more photo bioreactors (stage 90);
- Introducing cooled $CO_2$ and nitrogen oxides from at least one storage/cooling vessel for water desalination (stage 91);
- Harvesting algae from the bioreactors (stage 92); and
- Producing energy from the biomass of harvested algae (stage 93).

Figure 7:
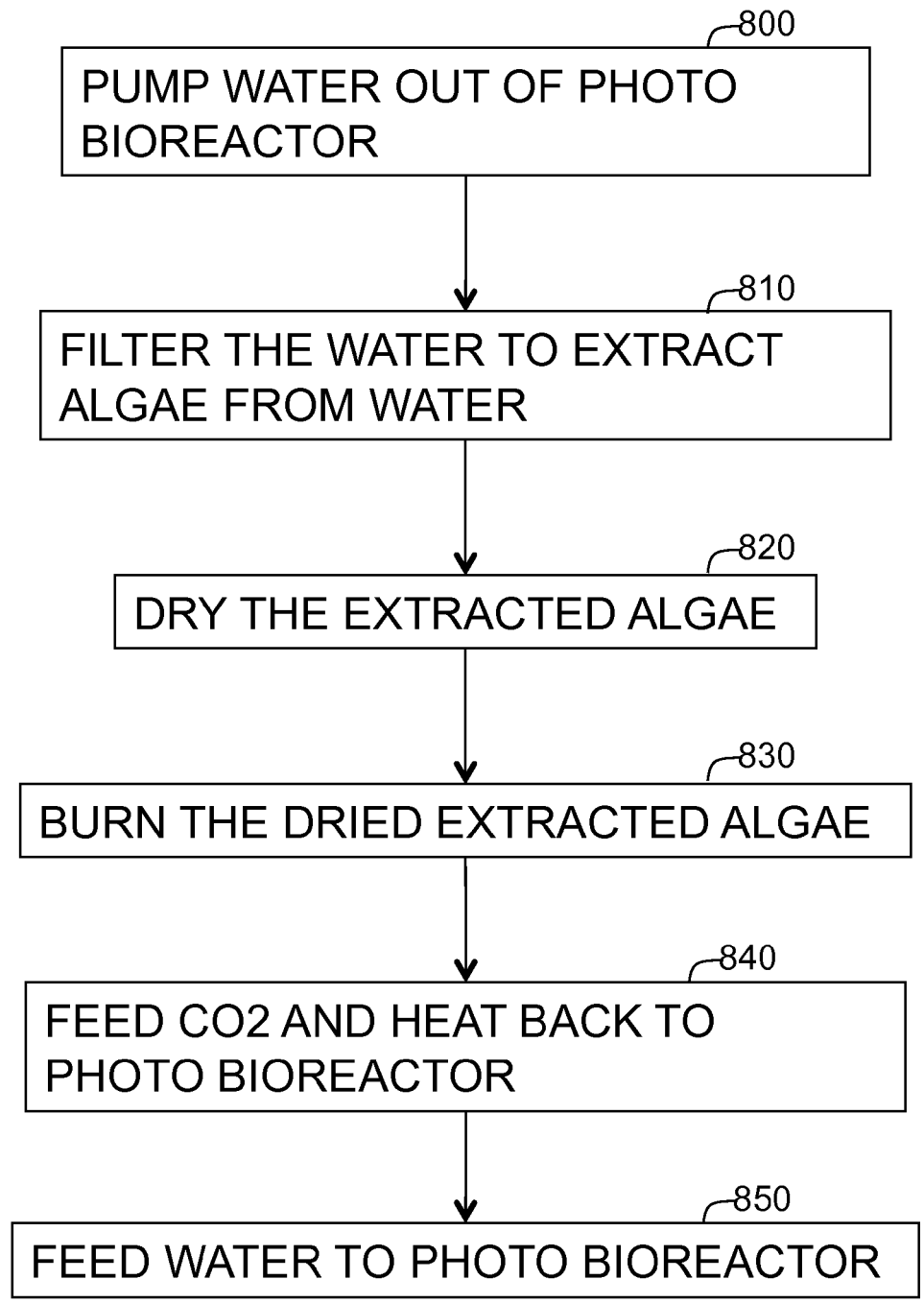
FIG. 7 is a flowchart illustrating a method of harvesting algae from the bioreactors according to some embodiments of the invention.

FIG. 7 is a flowchart illustrating a method of harvesting algae from the bioreactors (stage 92), according to some embodiments of the invention. The method comprises the stages:
- Pumping water out of photo bioreactor (stage 800);
- Filtering the water to extract algae from it (stage 810);
- Drying extracted algae (stage 820); and
- Burning said dried extracted algae (stage 830).

According to some embodiments of the invention, the method further comprises feeding at least part of $CO_2$ and heat resulting from burning dried extracted algae (stage 830) back into at least one of the photo bioreactors (stage 840).

According to some embodiments of the invention, the method further comprises feeding at least part of the water extracted during filtration of the extracted algae (stage 820) back into at least one of said photo bioreactors (stage 850). A control mechanism regulates the algae cell density and the rate of cell harvesting to be equal to the algae growth rate.

Figure 8:
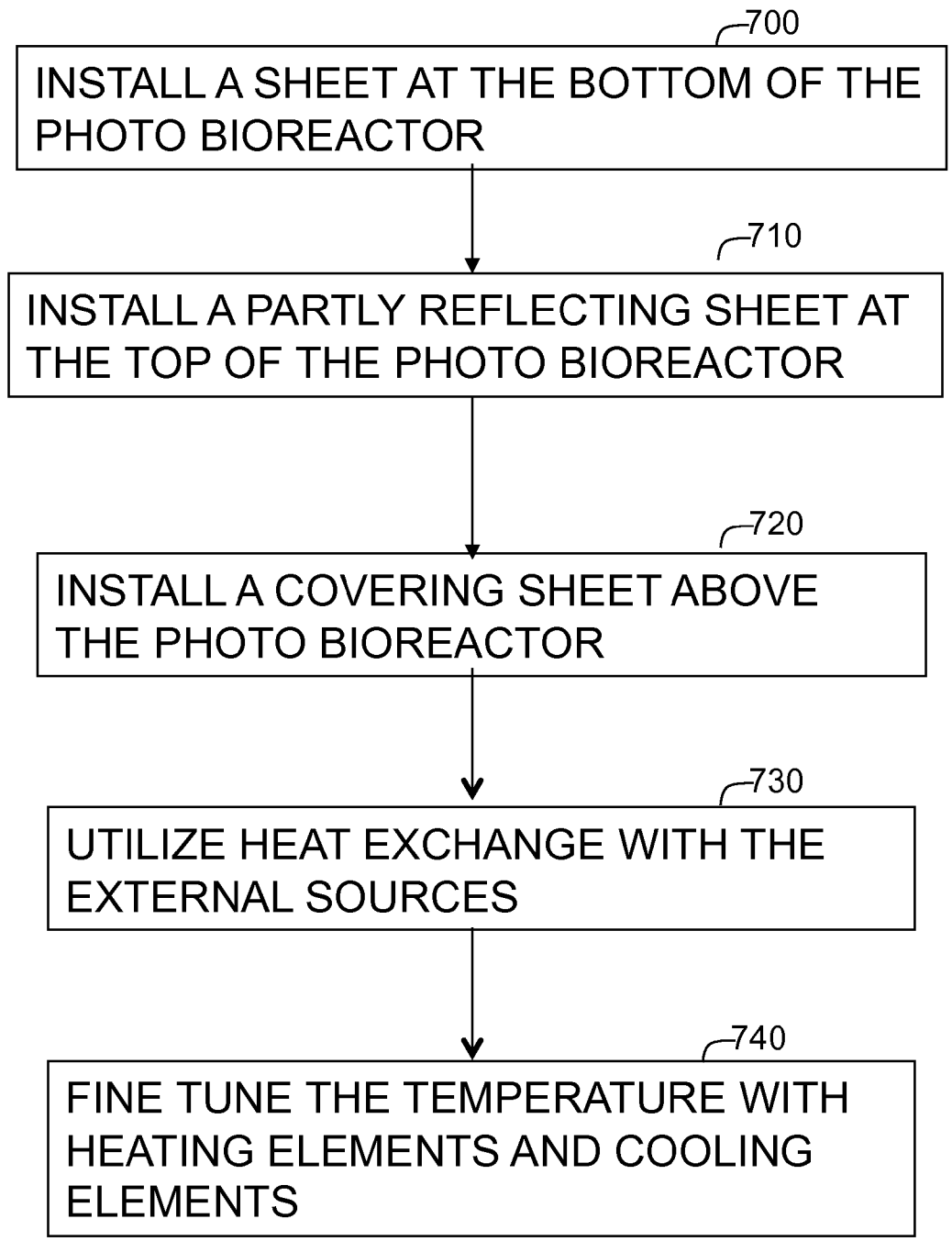
FIG. 8 is a flowchart illustrating optional stages in a stage of sustaining and regulating an algae culture in photo bioreactors according to some embodiments of the invention.

FIG. 8 is a flowchart illustrating optional stages in a stage of sustaining and regulating an algae culture in photo bioreactors (stage 90), according to some embodiments of the invention. The stage of sustaining and regulating an algae culture in photo bioreactors (stage 90) may comprise any of the following stages or a combination of these stages:
- Installing a sheet at the bottom of the photo bioreactor (stage 700);
- Installing a partly reflecting sheet at the top of the photo bioreactor (stage 710);
- Installing a covering sheet above the photo bioreactor (stage 720);
- Utilizing heat exchange with the external sources (stage 730); and
- Fine tuning of the temperature with heating elements and cooling elements connected to the photo bioreactor (stage 740).

The above calculations indicate that energy problems of the globe are not quantitative as long as the sun rises and enough area is available to absorb sunlight by the photosynthetic cells. The current invention suggests some solutions for both aspects of these energy problems. When oil is extracted from cells (about 50% of the cell dry weight) and is transesterified, too much energy is consumed for the production of the fuel (biodiesel), and too large part of the energy content of the cell is not extracted and lost. Consequently, no net energy (or only small amount of energy) is left. Therefore it is preferred to fuel kilns (for $CO_2$ production and other processes) with cells instead of fossil fuel. Most of the air is nitrogen, more than 79%, so there is no lack of this resource. On the other hand, the concentration of $CO_2$ in the air is only 0.03%, too low to enable "bioenergy" production in appropriate rate. If it is wished to reduce consumption of fossil fuels, or to save them for other utilities such as row materials for petro chemical industries, another source of $CO_2$, except fossil fuel, must be found. Almost all of the $CO_2$ on the surface of world had been deposited as limestone. The carbon in the limestone is not utilizable by the cells due to the low solubility of limestone and the negative free energy of the reaction between calcium and bicarbonate ions. Limestone is an endless resource of carbon for useful energy production. Fortunately the energy required to release the $CO_2$ from limestone is not too high, and the direction of the process can be reversed by the sunlight energy captured by the photosynthetic cells. The by product and by benefit of this process is quicklime, cement and desalinated water, which are produced by sunlight energy (mediated by cells) without any energy cost.

Even if cyclic systems with photosynthetic cells as discussed above are very efficient for sunlight energy transmission per each mass unit, the overall capacity of such systems may be too small, not because of lack of energy. The sunlight energy is supplied in huge excess, and only a tiny part of this energy can be used by us. The limiting factor is enough amount of material to transfer it. The amount and the concentration of $CO_2$ in the air are too small to do it with the required amount and rate. The amount of carbon in the atmosphere (in the form of $CO_2$) is estimated as 750 billions ton of carbon. The annual amount of carbon released to the atmosphere by fossil fuel combustion is about 5.5 billions ton of carbon, and this amount is increasing geometrically each year. If the fossil fuel has to be replaced by fuel which is produced by photosynthetic cells, we have to supply those photosynthetic cells with carbon ($CO_2$) in a similar rate of 5.5 billions tons of carbon per year. If this amount has to be supplied by the atmosphere, it is relatively a significant part of its carbon content: 5.5/750=1/136.4=0.73% of the overall carbon in the air. Taking into account that the $CO_2$ is dispersed all over the atmosphere, only a very small amount of this $CO_2$ is available to photosynthesis and the annual supply by the atmosphere is too small. According to various reports, the global amount of $CO_2$ which is absorbed by the oceans and the biosphere per year is about half of the annual amount of $CO_2$ which is released to the atmosphere. Consequently, the rate and the amount of $CO_2$ that the atmosphere can supply are much lower then what is needed for fuel production by photosynthetic cells. For that reason, the sunlight energy stored by the photosynthetic cells is transferred to an endless source of utilizable carbon (limestone) in order to amplify the amount of $CO_2$ needed to enhance the capacity of the system. A cyclic process amplified by $CO_2$ is not only an efficient way to supply energy; it is apparently the only possible way to supply energy in appropriate quantities and rate by photosynthetic cells in a large (global) scale. Let's assume that we have produced by sun energy an amount of fuel on a large scale, burned it, and the waste product has been dispersed to the environment. Where another similar amount of $CO_2$ can come from? The amount and concentration of $CO_2$ in the atmosphere is too small. There is an endless source of $CO_2$ (limestone), but we need energy to use it. For the time being, this $CO_2$ is released by fossil fuel, but this is exactly what we are trying to prevent. The only way to get out of this "Catch $CO_2$" is by keeping the waste products within the system for reuse, combined with $CO_2$ amplification by limestone firing.

According to some embodiments of the invention, the quantity of $CO_2$ released from burning algae and limestone may allow growing 3.44 times the algae burnt. The system actually produces desalinated water and clinker from limestone utilizing solar energy in the mediation of algae. The system accumulated biofuel in the form of algae to an amount exceeding manifolds the consumed amount of fuel. The source of carbon is $CO_2$ from limestone and the source of energy is the sun. The energy surplus may be consumed to produce electricity etc. The system does not emit $CO_2$ but recycles carbon and nitrogen sources. The system may increase its energy production geometrically, as long as area and limestone are available. The system is simple and requires cheap materials, yet produces unlimited amounts of energy, thus reducing fuel prices.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention can be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Those skilled in the art will envision other possible variations, modifications, and applications that are also within the scope of the invention. Accordingly, the scope of the invention should not be limited by what has thus far been described, but by the appended claims and their legal equivalents.

What is claimed is:

1. A system comprising:
   an array of photo bioreactors arranged to produce wet algae;
   an array of cell dryers arranged to receive said wet algae produced by the array of photo bioreactors and dry the wet algae to produce dry or pyrolyzed algae from the produced wet algae, and flue gas;
   at least one kiln arranged to produce cement or quicklime from limestone or dolomite, the at least one kiln capable of being heated by burning said dry or pyroglazed algae produced by the array of cell dryers, and is arranged to supply hot flue gas to the cell dryers;

an ammonia production plant heated by burning said dry or pyrolyzed algae produced by the array of cell dryers, and further arranged to supply hot flue gas to the cell dryers;

a desalination module arranged to condense desalinated water from the flue gas obtained from the cell dryers, after being cooled in a specified vessel; and a stripping device arranged to:
  receive ammonia from the ammonia production plant which flows in one direction and flue gas which flows from the photo bioreactors in an opposite direction;
  enable a chemical reaction between the ammonia and residual nitrogen oxides and CO2 contained within the flue gas to yield nutrients; and
  supply the photo bioreactors with the nutrients and the ammonia, wherein the array of photo bioreactors, the at least one kiln, the ammonia production plant, and the stripping device operate in a closed cyclic process that yields accumulated amounts of algae.

2. A method comprising:

producing wet algae within an array of photo bioreactors;

drying said produced wet algae in an array of cell dryers to produce dry or pyrolyzed algae from the produced wet algae, and flue gas;

producing cement or quicklime from limestone or dolomite in at least one kiln being heated by burning said dry or pyrolyzed algae;

supplying hot flue gas from the at least one kiln to the cell dryers;

heating an ammonia production plant by burning said dry or pyrolyzed algae, to yield a supply of hot flue gas to the cell dryers;

condensing desalinated water from the flue gas obtained from the cell dryers by cooling the hot flue gas in a specified vessel in operative association with a desalination module;

receiving ammonia from the ammonia production plant which flows in one direction and flue gas which flows from the cell dryers in an opposite direction;

enabling a chemical reaction between the ammonia and residual nitrogen oxides and CO2 contained within the flue gas from the cell dryers to produce nutrients; and supplying the photo bioreactors with said produced nutrients and the ammonia, wherein the array of photo bioreactors, the at least one kiln, the ammonia production plant, and the stripping device operate in a closed cyclic process that yields accumulated amounts of algae.

* * * * *